United States Patent
D'Arcangelo et al.

(10) Patent No.: US 8,540,739 B2
(45) Date of Patent: Sep. 24, 2013

(54) ANASTOMOTIC DEVICE

(75) Inventors: Michele D'Arcangelo, Rome (IT); Jesse J. Kuhns, Cincinnati, OH (US); Alessandro Pastorelli, Rome (IT); Federico Bilotti, Aprilia (IT); Roberto Tacchino, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 682 days.

(21) Appl. No.: 12/159,002

(22) PCT Filed: Jan. 11, 2007

(86) PCT No.: PCT/EP2007/000194
§ 371 (c)(1),
(2), (4) Date: Dec. 7, 2009

(87) PCT Pub. No.: WO2007/080110
PCT Pub. Date: Jul. 19, 2007

(65) Prior Publication Data
US 2010/0069932 A1    Mar. 18, 2010

(30) Foreign Application Priority Data
Jan. 16, 2006  (IT) .............................. MI2006A0062

(51) Int. Cl.
*A61B 17/08* (2006.01)
(52) U.S. Cl.
USPC ......................................... 606/153; 606/213
(58) Field of Classification Search
USPC ........................ 606/108, 139, 151, 153, 213
See application file for complete search history.

(56) References Cited

U.S. PATENT DOCUMENTS

| 3,316,914 | A | * | 5/1967 | Collito ........................... 606/150 |
| 4,233,981 | A | * | 11/1980 | Schomacher ................. 606/153 |
| 5,035,702 | A |  | 7/1991 | Taheri |
| 5,250,058 | A |  | 10/1993 | Miller et al. |
| 5,336,233 | A | * | 8/1994 | Chen ............................. 606/153 |
| 5,626,590 | A | * | 5/1997 | Wilk ............................. 606/148 |
| 6,543,456 | B1 |  | 4/2003 | Freeman |
| 6,569,173 | B1 |  | 5/2003 | Blatter et al. |
| 6,652,540 | B1 | * | 11/2003 | Cole et al. ..................... 606/153 |
| 2001/0016749 | A1 | * | 8/2001 | Blatter et al. ................. 606/153 |
| 2003/0216749 | A1 |  | 11/2003 | Ishikawa et al. |
| 2004/0102779 | A1 | * | 5/2004 | Nesper et al. .................. 606/72 |
| 2004/0186489 | A1 |  | 9/2004 | Lee |
| 2004/0225191 | A1 |  | 11/2004 | Sekine et al. |
| 2005/0277962 | A1 |  | 12/2005 | Myers |
| 2006/0004392 | A1 | * | 1/2006 | Amarant ....................... 606/153 |

FOREIGN PATENT DOCUMENTS

EP    1 317 908 A2    6/2003
WO   WO 0078226 A1 *  12/2000

* cited by examiner

*Primary Examiner* — Corrine M McDermott
*Assistant Examiner* — Robert A Lynch

(57) ABSTRACT

An anastomotic device (10) is suitable for approximating and keeping close to each other a first tissue portion (12) and a second tissue portion (14) intended to form an anastomosis. The anastomotic device (10) comprises an abutment portion (18) suitable for the abutment against a surface of the first tissue portion (12) and a locking portion (20) suitable for being placed opposite the abutment portion (18) with respect to the first and second tissue portion (12, 14). The locking portion (20) and the abutment portion (18) are mutually connectable through the first and second tissue portions approximated, to keep them connected. The anastomotic device (10) is suitable for being connected to a guide means comprising at least one guide wire (A, B).

2 Claims, 38 Drawing Sheets

FIG..26

ANASTOMOTIC DEVICE

The present invention generally relates to devices for use in methods for performing anastomoses in tracts of the digestive tube. In particular, these devices are suitable for performing anastomoses endoluminally, even if they can be used in partially or wholly laparoscopic techniques or in conventional surgery techniques.

In accordance with a first aspect, it is an object of the present invention an anastomotic device suitable for approximating and possibly keeping close to each other a first tissue portion and a second tissue portion that are intended to form an anastomosis. The aforesaid anastomotic device is particularly suitable for being applied endoluminally, even if its use is possible in partially or wholly laparoscopic techniques or in conventional surgery techniques.

According to a further aspect, the present invention relates to a kit further comprising a positioning device to deploy at least one portion of an anastomotic device suitable for approximating and keeping close to each other a first tissue portion and a second tissue portion that are intended to form an anastomosis. Also this device is particularly suitable for being used endoluminally, even if its use is possible in partially or wholly laparoscopic techniques or in conventional surgery techniques.

The known devices are quite invasive and need the use of positioning devices that are quite complex and bulky. Furthermore, the known devices do not allow an endoluminal, or at least partially endoluminal, approach.

As it is known, the endoluminal approach considerably minimizes the drawbacks of the conventional surgical or laparoscopic methodology. In particular, it allows minimizing the invasiveness of the procedure, thus decreasing the risks for the patient and shortening the post-operative course.

It is currently extremely difficult to utilize the endoluminal approach to perform anastomoses in tracts of the digestive tube, in particular due to the lack of equipment suitable to this aim. Consequently, the anastomoses of tracts of the digestive tube, for example to perform gastro-intestinal bypasses, are still conducted through conventional surgical or laparoscopic techniques.

The problem at the heart of the present invention is to propose devices for use in methods to perform anastomoses in tracts of the digestive tube, which allow to solve the drawbacks cited with reference to the prior art.

A further problem at the heart of the present invention is to propose devices usable in methods to perform anastomoses in tracts of the digestive tube that are particularly suitable for endoluminal use, thus allowing to meet the increasing need to widen the utilization fields for this technique, while being also suitable for use in partially or wholly laparoscopic techniques or in conventional surgery techniques.

This problem is solved by means of an anastomotic device in accordance with claim 1.

Further features and advantages of the device according to the invention will be understood from the description set forth herein below of preferred and exemplificative embodiments, given by way of non-limiting illustration, with reference to the attached Figures, in which.

Figure 30:
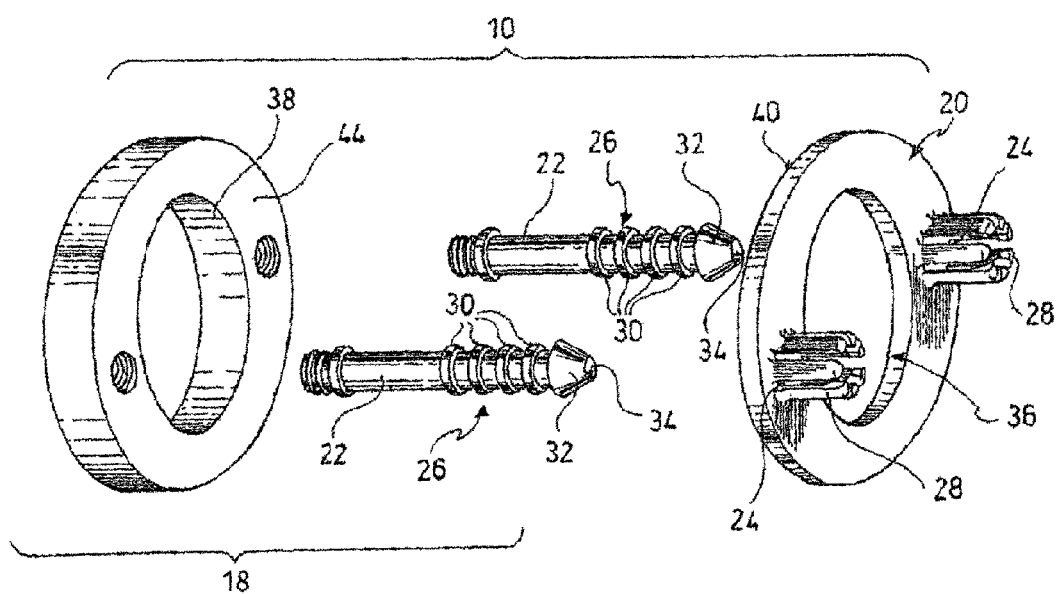
FIG. 30 illustrates a perspective and exploded view of an anastomotic device according to the present invention suitable for being used in some steps of the method.

Referring to FIG. 30, an anastomotic device has been generally indicated with 10. FIGS. 18-28, 33, and 34 illustrate possible applications of the anastomotic device 10 or variant embodiments thereof.

In accordance with a first embodiment, the anastomotic device according to the present invention is suitable for approximating and keeping close to each other a first tissue portion 12 and a second tissue portion 14 that are intended to form an anastomosis 16. More particularly, the anastomotic device 10 is suitable for being used in a method, preferably endoluminally, for performing anastomoses in tracts of the digestive apparatus. However, it is optionally possible its use in partially or wholly laparoscopic techniques or conventional surgical techniques.

FIG. 30 illustrates an exploded view of a preferred embodiment of the anastomotic device 10 in which an abutment portion has been indicated with 18 and a locking portion has been indicated with 20. Referring in particular to the application of the anastomotic device 10 in a method for the performance of a gastro-jejunostomy (G-J), or similar methodologies, the abutment portion 18 can also be defined as the intestinal portion, while the locking portion 20 can also be defined as the gastric portion.

The abutment portion 18 is suitable for abutting against a surface of the first tissue portion 12, while the locking portion 20 is adapted to be arranged opposite the abutment portion 18 with respect to the first tissue portion 12 and to the second tissue portion 20.

In accordance with a general embodiment of the invention, the locking portion 20 and the abutment portion 18 are mutually connectable or couplable by the first and second tissue portions being drawn together, in order to keep them joined to each other. More particularly, the locking portion 20 and the abutment portion 18 are suitable for being mutually locked in at least two locking positions corresponding to different compression degrees of the first and second tissue portions.

In accordance with a preferred embodiment, the abutment portion 18 comprises at least one pin 22 suitable for passing through the first tissue portion 12 and the second tissue portion 14 and to fit in a housing 24 of the locking portion 20 in order to fit thereto.

Preferably the pin is adapted to snap fit and lock within the housing 24 of the locking portion 20. The snap fit is for example carried out by means of a pin 22 provided with at least one shaped portion 26 suitable for defining a snap connection with elastic tabs 28 associated to the respective housing 24 of the locking portion 20. Preferably, the elastic tabs 28 extend in the direction of the respective pin 22 away by the abutment portion 18 in order to extend the housing 24.

In the preferred embodiment as illustrated in FIG. 30, the shaped portion 26 is provided by means of a sequence of ring ribs 30. Furthermore, a free end of the pin 22 is shaped so as to promote the snap fitting, for example providing an outwardly tapering or frusto-conical end 32. Furthermore, the elastic tabs 28 are distributed along a peripheral edge of the respective housing 24 and extend in the insertion direction and sense of the pin 22.

In accordance with a preferred embodiment, the pin 22 is movably mounted, preferably screwed, to the abutment portion 18.

In accordance with a preferred embodiment, the pin 22 defines internally a channel 34 opened on both sides and preferably adapted to receive a guide wire, as it will be described herein below. In accordance with this embodiment, also the respective housing 24 is adapted to receive the guide wire passing through the channel 34.

Referring to the annexed Figures, which illustrate a preferred embodiment of the invention, and in particular to FIG. 30, the anastomotic device 10 comprises two pins 22, as described above, which extend from the abutment portion 18 and are adapted to fit in respective housings 24 of the locking portion. Preferably, the pins are located at opposite areas or sides of the abutment portion 18 and, similarly, the housings adapted to receive the pins are located at opposite areas or sides of the locking portion 20. When two pins are provided, as illustrated in the Figures, it is particularly advantageous that each pin defines a channel 34 therein, which is adapted to receive a respective guide wire.

Optionally, two or more pins can be provided, as described above. If the number of pins corresponds to the number of the guide wires, each pin defines a channel 34 to receive a respective guide wire therein.

According to a possible embodiment, the locking portion 20 presents an opening 36 to access the area intended for the formation of the anastomosis. In the case where two housings 24 are provided, these are located at opposite parts or sides of the opening 36. Preferably, the locking portion 20 is essentially ring-shaped.

Similarly, the abutment portion 18 presents an opening 38 to access the area intended for the formation of the anastomosis and corresponding to the opening 36 of the locking portion. When two pins 22 are provided, these are preferably located at opposite parts or sides of the opening 38. Also the abutment portion 18 is, preferably, essentially ring-shaped.

Figure 33:
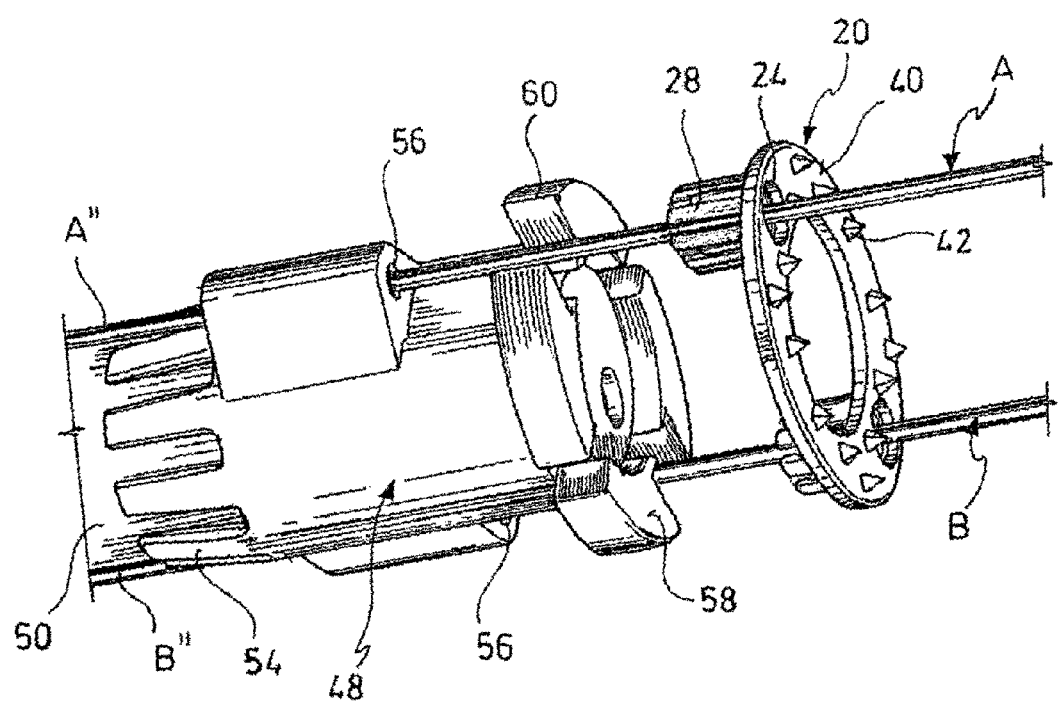
FIG. 33 illustrates a perspective view of the positioning device of FIG. 32 according to a different point of view and associated to a variant embodiment of a portion of the anastomotic device of FIG. 30.
Figure 34:
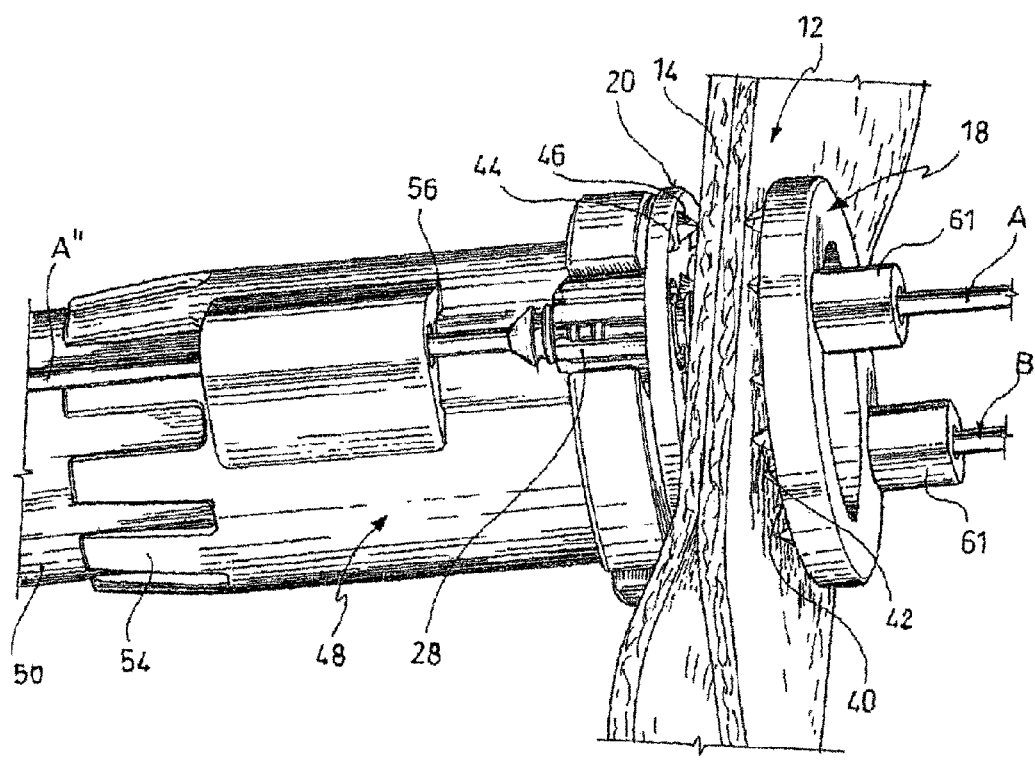
FIG. 34 illustrates a perspective view of a step of the method, carried out with a variant embodiment of the anastomotic device illustrated in FIG. 30.
Figure 37:
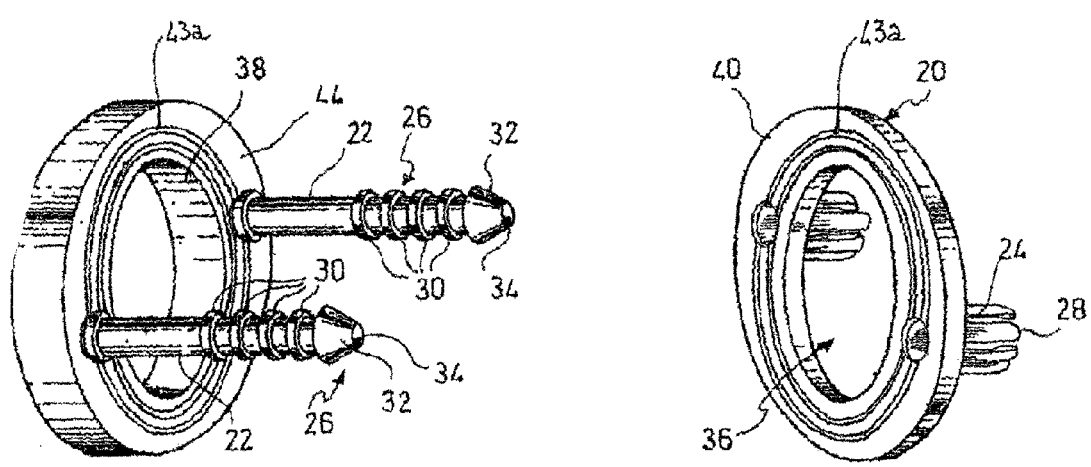
FIG. 37 illustrates a possible variant embodiment of a device.
Figure 38:
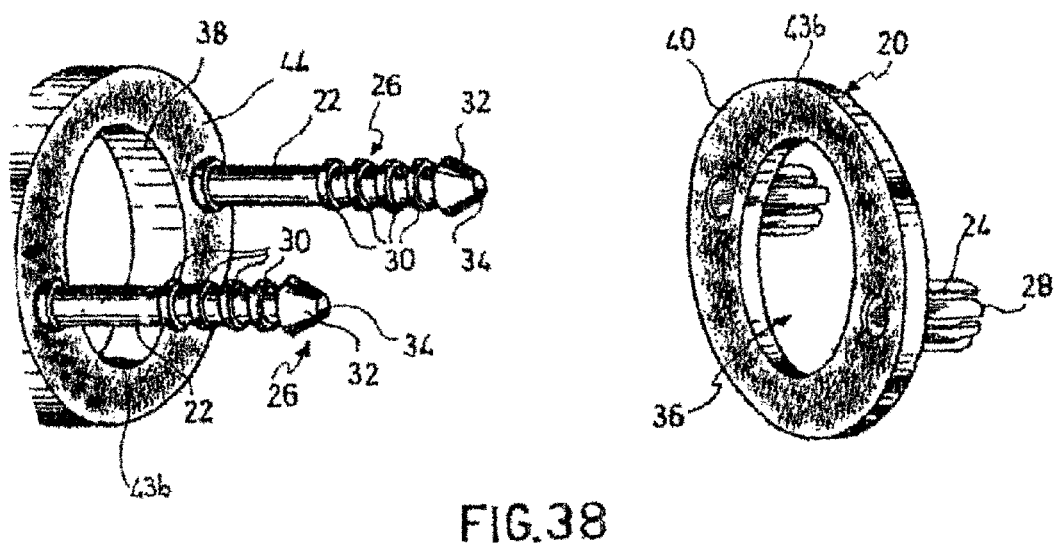
FIG. 38 illustrates a possible further variant embodiment of an anastomotic device.

A contact surface of the locking portion 20 suitable for the abutment against a surface of the second tissue portion 14 to be drawn close has been indicated by 40. This contact surface is a surface opposite to the deployment of the elastic tabs 28, where present. In accordance with a preferred embodiment, the contact surface 40 is rough or presents pointed members 42 (FIGS. 33 and 34). Optionally, annular grooves 43a can be provided (FIG. 37) or, the roughness can be imparted through a layer 43b made of material reported for example in granular form (FIG. 38).

According to a possible embodiment, a contact surface of the abutment portion 18 suitable for the abutment against a surface of the first tissue portion 12 to be drawn close has been indicated with 44. In case at least one pin is provided, this contact surface is a surface located on the same side as the at least one pin 22. In accordance with a preferred embodiment, the contact surface 44 is rough or presents pointed members 46 (FIG. 34). Optionally, annular grooves 43a can be provided (FIG. 37) or, the roughness can be imparted through a layer 43b made of material reported for example in granular form (FIG. 38).

Generally speaking, and according to a first aspect of the present invention, the anastomotic device 10 is a device suitable for approximating and keeping close to each other a first tissue portion and a second tissue portion that are intended to form an anastomosis, which can be connected to a guide means, for example a guide wire or, preferably, at least two guide wires to reach the tissue portions, as it will be described below.

In particular, at least one of the abutment portion 18 and the locking portion 20 is suitable for being connected to a guide means comprising at least one guide wire to reach the first or second tissue portions.

Referring particularly to the annexed Figures, the abutment portion 18 is suitable for being locked in a direction on the guide means, for example the guide wires A and B, preferably located on two opposite sides of the anastomotic device, through which it is dragged until reaching the first tissue portion 12. In other terms, the constraint between the abutment portion 18 and the guide wires allows to drag it to the first tissue portion and to use it to draw the two tissue portions together, thus allowing the guide wires to be withdrawn in the opposite direction.

Figure 17:
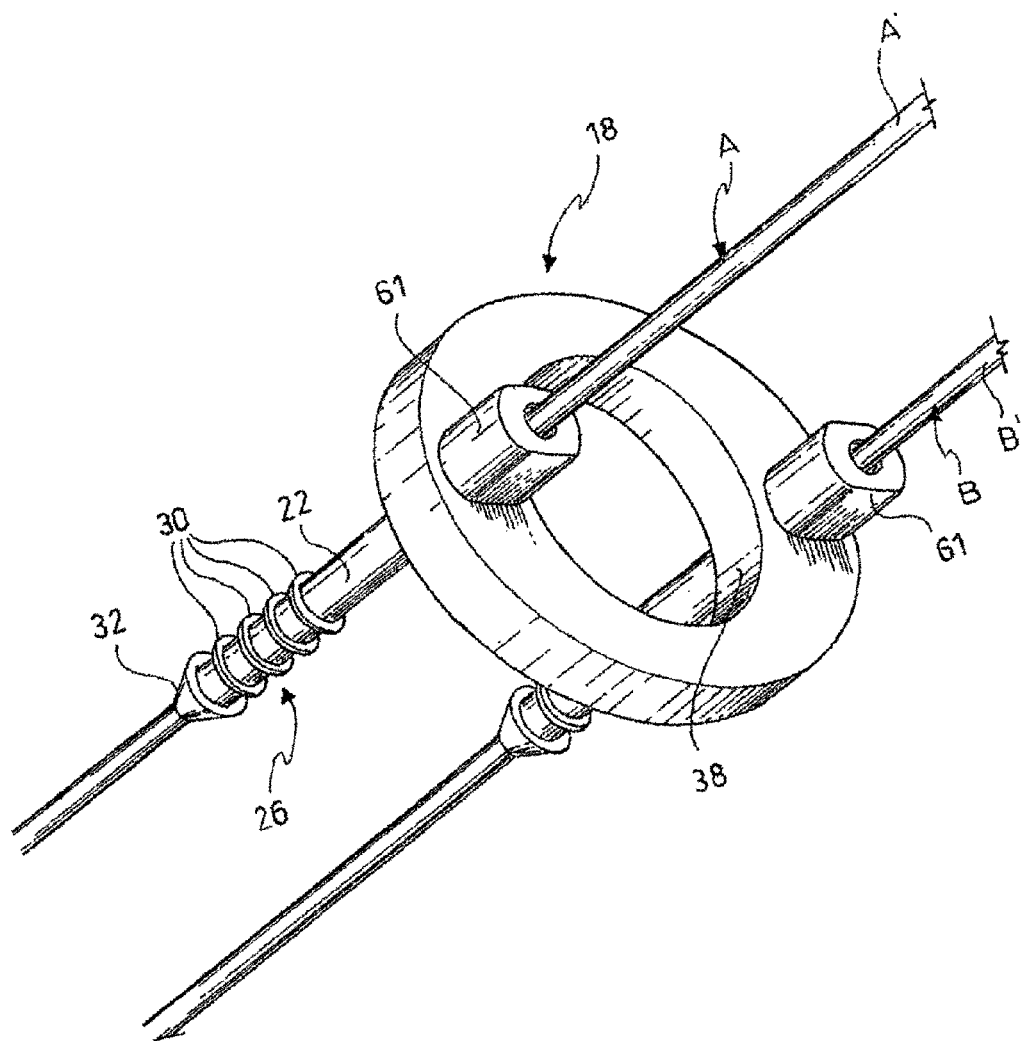
FIG. 17 illustrates a perspective view of a portion of an anastomotic device according to the present invention applied in a further step of the method.

In accordance with a possible embodiment, the abutment portion 18 is suitable for being locked on the guide wires A, B for example by means of locking members 61 made integral respectively to a guide wire and suitable for defining an obstacle for the sliding movement of the abutment portion 18 in a direction on the guide wires (FIG. 17).

In accordance with an advantageous embodiment, the abutment portion 18 comprises at least one channel adapted to receive a guide wire. When two guide wires are provided, two channels located on opposite sides of the anastomotic device are advantageously provided. Furthermore, it is advantageously provided that the channels are passed through the abutment portion 18.

In accordance with a possible embodiment, the guide means pass through the abutment portion 18 and the locking portion 20 at connecting members between the two portions. According to a preferred embodiment described above, in which the anastomotic device 10 comprises at least one pin in order to connect to the locking portion 20, it is advantageously provided that this pin 22 defines a channel 34 adapted to receive a guide wire. Particularly, according to a further preferred embodiment in which the anastomotic device 10 comprises at least two pins 22 to be connected to the locking portion, is advantageously provided that the two pins 22 define a channel 34 adapted to receive a guide wire, respectively.

In accordance with a preferred embodiment, the locking portion 20 is adapted to slide along the guide means and presents an interacting portion with a positioning device 48 which biases the latter along said guide means. Advantageously, also the positioning device 48 is adapted to slide along the guide means, (one or more guide wires) and comprises an elongated structure 50. In the illustrated examples, the elongated structure 50 consists in a visualization device, for example of the gastroscope kind.

According to a possible embodiment, particularly advantageous in the case of the visualization device, the positioning device 48 comprises a head 52 suitable for interference fitting on a distal end of the elongated structure 50 (visualization device). In accordance with a possible embodiment, the head 52 comprises elastic tabs 54 which extend from a proximal end of the same head.

In accordance with an embodiment, the head 52 comprises at least one channel 56 suitable for receiving a guide wire. In the case where the guide means comprises two or more guide wires, the head 52 comprises at least two channels 56 suitable for receiving a guide wire, respectively.

Furthermore, the head 52 comprises a distal end defining a thrust surface 58 for the locking portion 20. In the case where the locking portion 20 comprises housings 24 to receive guide wires and elastic tabs 28 in order to snap lock on the abutment portion 18, the distal end of the head 52 comprises at least one opening 60 to receive the elastic tabs of the locking portion. In the example illustrated in the Figures, two housings of the locking portion and two relative openings 60 of said head 52 are provided.

According to possible variations to what has been illustrated above, the head 52 can be applied to any kind of elongated structure.

It is clear that variations and/or additions to what has been described and illustrated above can be provided.

For example, the pins 22 can be made as one piece with the abutment portion 18. Or, the pins can extend from the locking portion 20 and fit in housings of the abutment portion 18.

The anastomotic device 10 can be made of any type of material suitable for surgical application. In addition to what has been stated above, in particular in the case of an anastomotic device 10 suitable both for approximating and keeping close to each other the tissue portions, both the abutment portion and the locking portion can be made in not-bioabsorbable material, for example in plastic or metallic material. In this case, the anastomotic device disengages and moves naturally away when the tissue to which it is attached necrotizes. According to a different embodiment, the anastomotic device can be made such as to stay in a steady position.

Alternatively, the choice of the material can be directed towards a bioabsorbable or biofragmentable material, thus providing that the anastomotic device is completely absorbed after a fixed time period.

Finally, the anastomotic device 10 can be partially made in bioabsorbable or biofragmentable material. In particular, it is advantageous to provide for the realization of the connecting members between the abutment portion and the locking portion in bioabsorbable or biofragmentable material, in order to allow the anastomotic device to disengage from the site to which it has been applied after a fixed time period and to naturally move away. In the case illustrated in the annexed drawings, it can be advantageously provided that the pins 22 and/or the housings 24 and/or the elastic tabs 28 are made in bioabsorbable or biofragmentable material.

An anastomotic device 10 according to the present invention suitable for approximating and keeping close to each other a first tissue portion 12 and a second tissue portion 14 that are intended to form an anastomosis 16 can generally be made in such a way that the abutment portion and the locking portion are mutually connectable through the first and second tissue portions approximated in order to keep them joined to each other. In particular, also a single pin 22 can be provided and optionally different from the housing channel of the guide wire. Furthermore, it can be provided that this anastomotic device can be fitted and is lockable even on a single guide wire or on more than two guide wires.

Optionally, the abutment portion 18 can be pre-assembled or integral with the at least one guide wire. The connection between the at least one guide wire and the abutment portion 28 can be done in such a way that the guide wires are removed at the end of the procedure.

According to a further aspect, the present invention relates to an anastomotic device 10 suitable for approximating a first tissue portion 12 and a second tissue portion 14 that are intended to form an anastomosis. According to such aspect, the anastomotic device comprises an abutment portion 18 suitable for the abutment against a surface of the first portion 12 to be approximated suitable for being connected to at least two guide wires to reach the first tissue portion. Preferably, the abutment portion 18 is suitable for being locked in a direction on the guide wires through which it is dragged until reaching the first tissue portion.

What has been described above with reference to the abutment portion is applicable also to the anastomotic device according to this further aspect. In particular, the abutment portion is suitable for being locked in a direction on at least two guide wires located on two opposite sides of the device and can have a contact surface 44, as described above, suitable for being abutted against a surface of the first tissue portion 12 to be drawn closer.

Advantageously, the abutment portion 18 comprises at least two channels 34 suitable for receiving a guide wire, respectively, which are preferably located on opposite sides of the anastomotic device. According to a possible embodiment, the channels 34 pass through the abutment portion 18.

Advantageously, the abutment portion comprises at least one pin, preferably two pins 22 which extend from the same abutment portion. Preferably, at least one pin 22 defines a channel 34 therein, which is suitable for receiving a guide wire. In particular, the pins 22 are movably mounted to the abutment portion, preferably screwed.

In accordance with a possible embodiment, the pins 22 are suitable for passing through the first tissue portion 12 and the second tissue portion 14.

The device according to the latter further aspect of the present invention, is anyway suitable for carrying out an anastomotic device as described above, i.e.

suitable not only for approximating, but also keeping close to each other a first tissue portion 12 and a second tissue portion 14 that are intended to form an anastomosis 16. For example, the pins 22 (or the at least one pin) can be suitable for the coupling with a locking portion 20 such as described above. In this case also, it is possible to provide the use of a positioning device 48, as described above, to locate the locking portion 20.

It is described below the mode of use of an anastomotic device according to the preferred embodiments illustrated and according to the two above described aspects of the invention. The application example refers to a method for performing anastomoses in tracts of the digestive tube, and in particular to a method for performing endoluminally a gastro-jejunostomy, for example as illustrated in FIGS. 18-28. Other applications are possible, such as a jejuno-jejunostomy, generally an entero-entero anastomosis or other kinds of anastomosis.

Figure 18:
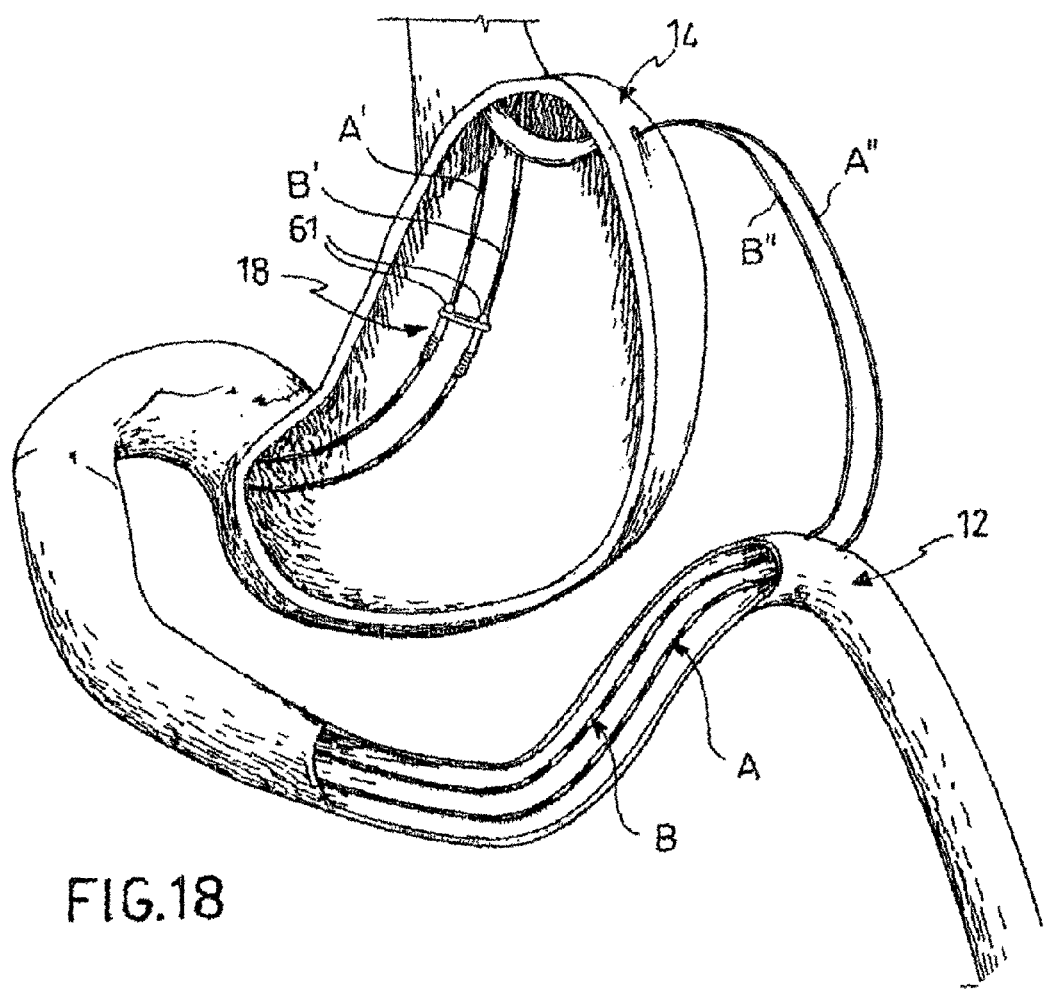
FIG. 18 illustrates a further step of the method carried out on the portion of FIG. 16.
Figure 19:
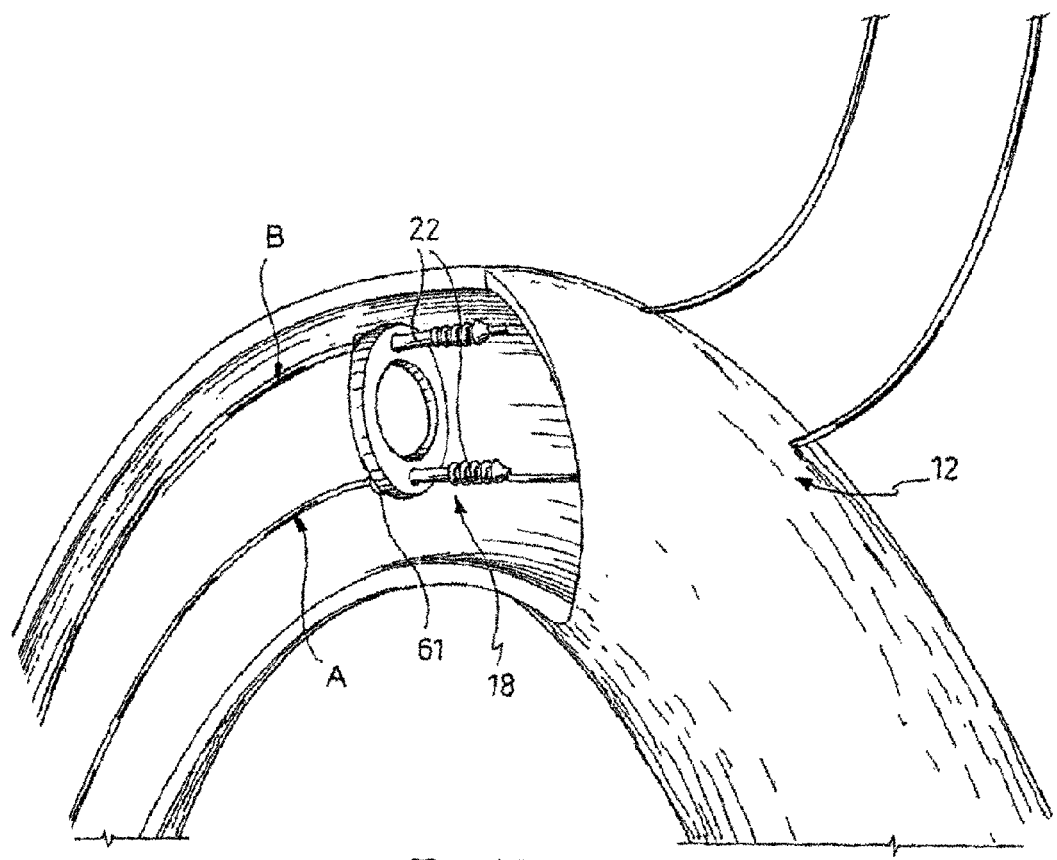
FIGS. 19 and 20 illustrate perspective and enlarged views of a detail from FIG. 18 respectively corresponding to further steps of the method.

In FIG. 18 a portion of the digestive apparatus comprising stomach and an intestine tract, corresponding to a jejune tract is illustrated. A guide means for example comprising two guide wires has been located starting from a natural orifice, such as the oesophagus, and forms an open ring or loop which passes through the first tissue portion 12 and the second tissue portion 14.

The two guide wires A and B extend between proximal end portions A' and B' and distal end portions A" and B". The abutment portion 18 of the anastomotic device 10 is fitted on proximal end portions of the guide wires and locked in a direction, for example by means of the locking members 61 that are respectively made integral to a guide wire and suitable for defining an obstacle to the sliding in a direction of the abutment portion 18 on said guide wires (FIG. 17). Alternatively, other locking means can be provided, for example integrated in the anastomotic device structure. Optionally, the abutment portion 18 is pre-connected or integral to the guide wires in such a way that when the distal ends of the guide wires are dragged, the abutment portion is dragged and approximated to the tissue portions to be connected.

Figure 20:
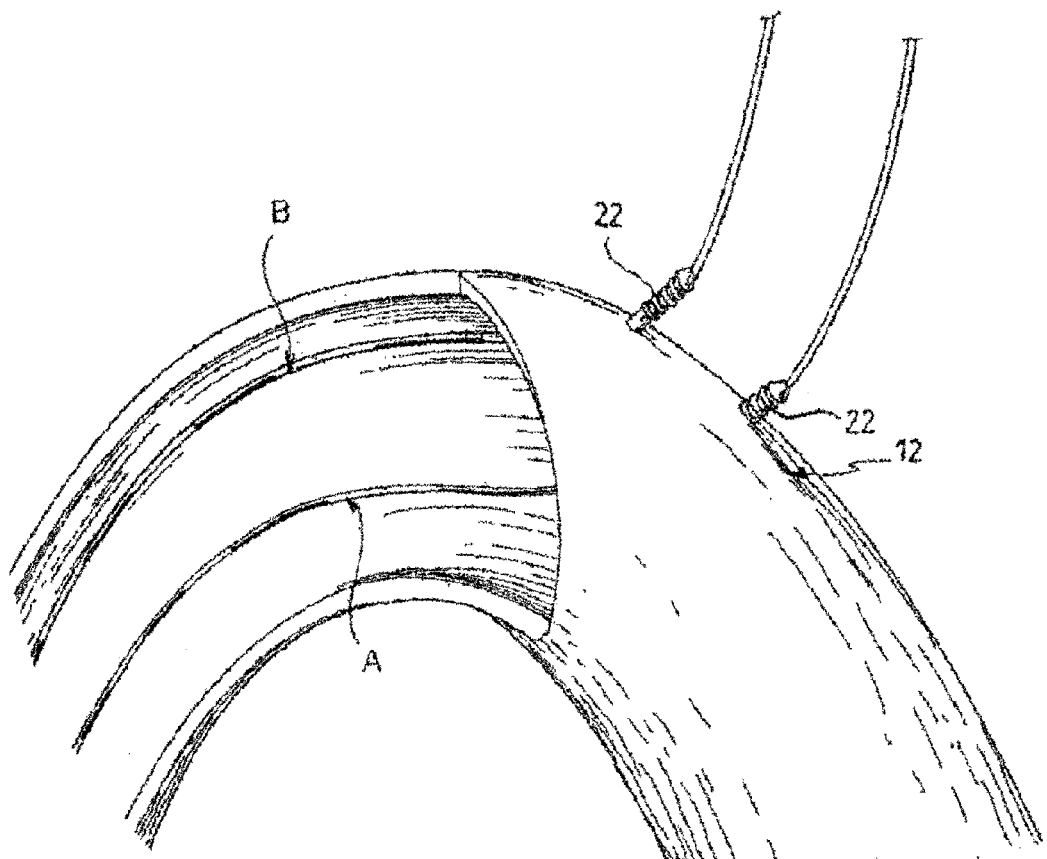

The abutment portion 18 is subsequently approximated to the first tissue portion 12 by pulling distal end portions of the guide wires (FIG. 19) until the pins 22 fit in and pass through the first tissue portion 12 (FIG. 20).

Figure 21:
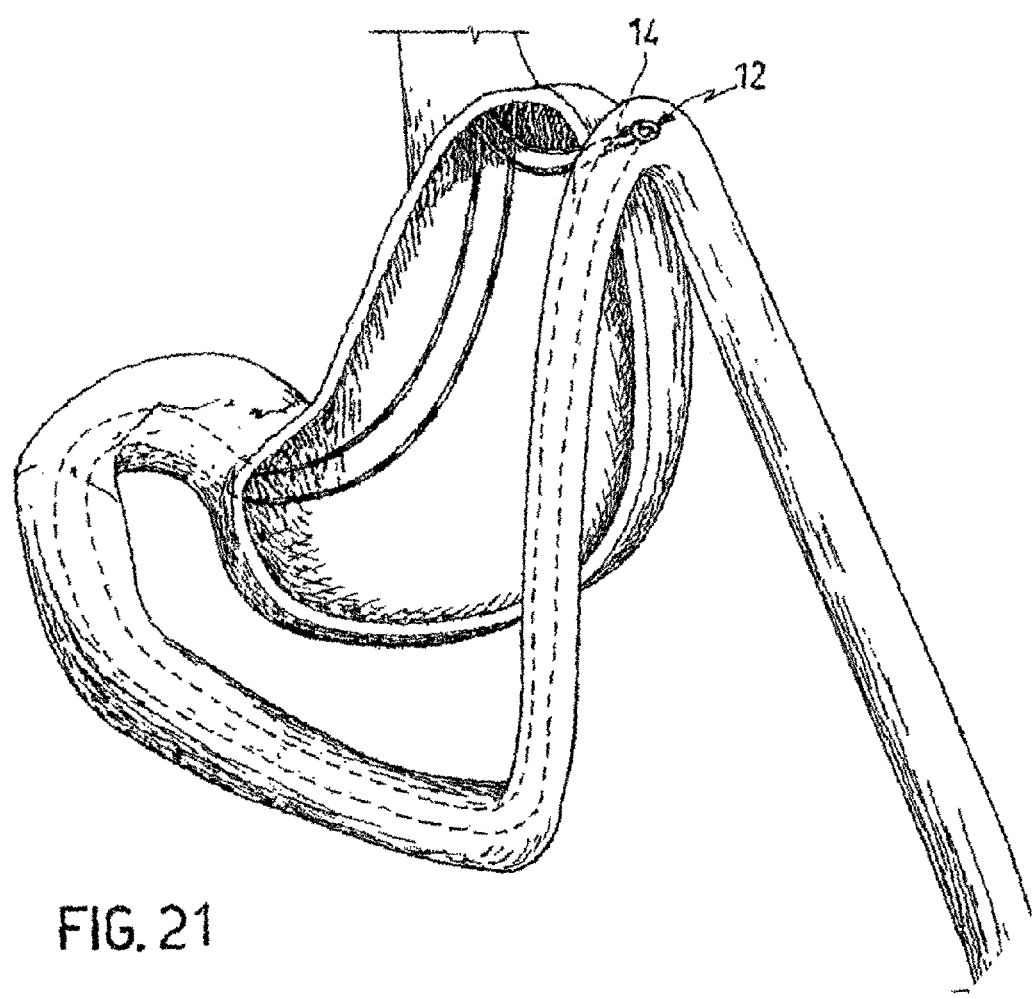
FIG. 21 illustrates a further step of the method carried out on the portion of FIG. 15.

The contact surface 44 abuts internally against the first tissue portion 12, therefore a further traction performed on the distal end portions of the guide wires causes the drawing of the first tissue portion 12, dragged by the abutment portion 18, together with the second tissue portion 14 (FIG. 21). In other terms, FIGS. 18-21 illustrate an application of an anastomotic device 10 according to one of the aspects of the invention, i.e. an anastomotic device suitable for approximating a first tissue portion and a second tissue portion that are intended to form an anastomosis.

Figure 22:
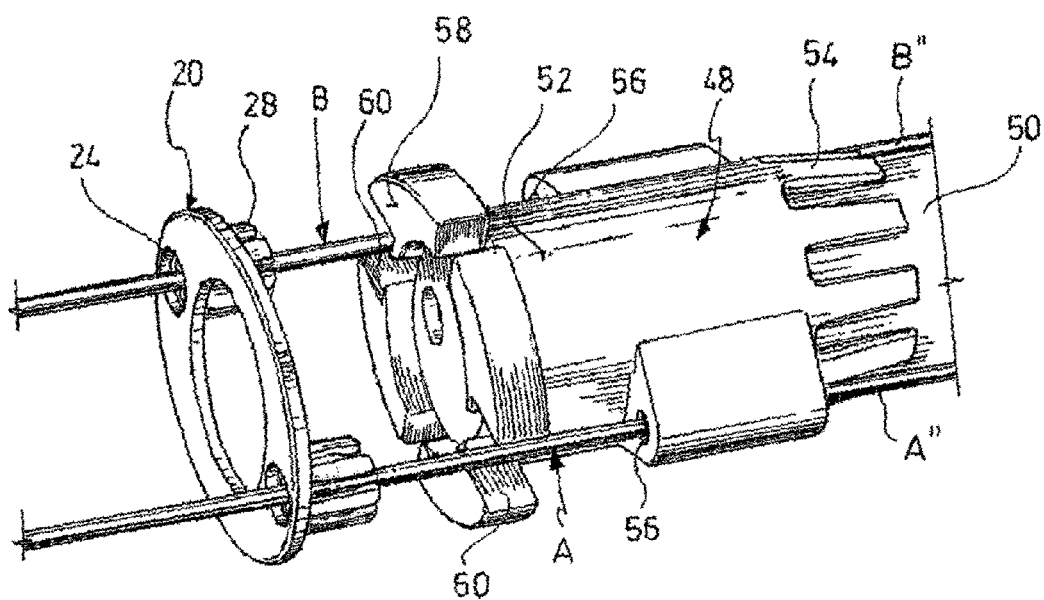
FIG. 22 illustrates a perspective view of a portion of an anastomotic device and of a positioning device, according to the present invention, applied in a further step of the method.

The advantageous conformation of the anastomotic device 10 makes it possible to be used as a device not only to approximate but also to keep close the two tissue portions to each other. This application is further illustrated in FIGS. 22-28, in which the application of the locking portion 20 is shown, preferably biased in position along the guide wires by the positioning device 48. The locking portion 20 is fitted on the distal end portions A" and B" of the guide wires through the housings 24. The head 52 is also subsequently fitted on the distal end portions of the guide wires through the channels 56. Finally, the head 52 is fitted on the distal end of the elongated structure 50, or gastroscope (FIG. 22). The positioning device 48 interacts with the locking portion 20 via the thrust surface 58 and the elastic tabs 28 fit in the respective openings 60.

Figure 23:
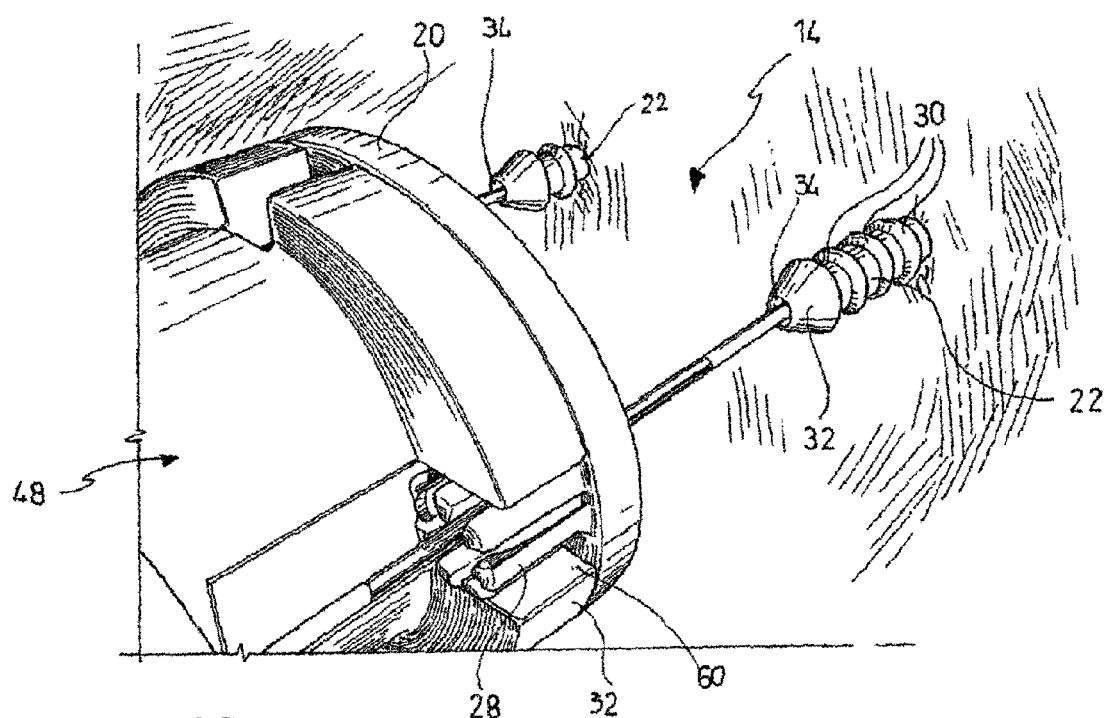
FIG. 23 illustrates a perspective view and from the interior of the stomach of a further step of the method.
Figure 24:
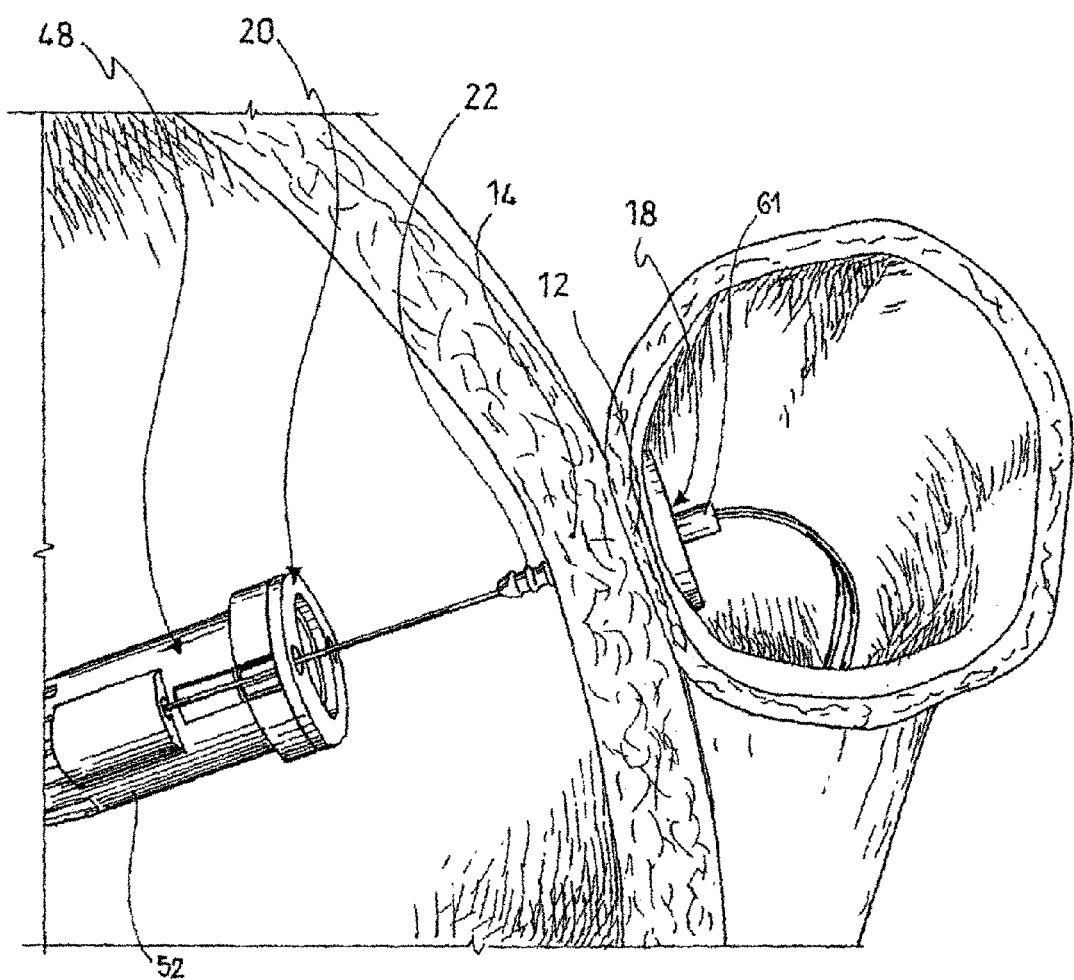
FIG. 24 illustrates the view from FIG. 23 according to a different point of view.

The head 52 biases the locking portion 20 in position by sliding on the guide wires until approaching to the second tissue portion 14, oppositely of the abutment portion 18, i.e. on the stomach side (FIGS. 23 and 24).

Figure 25:
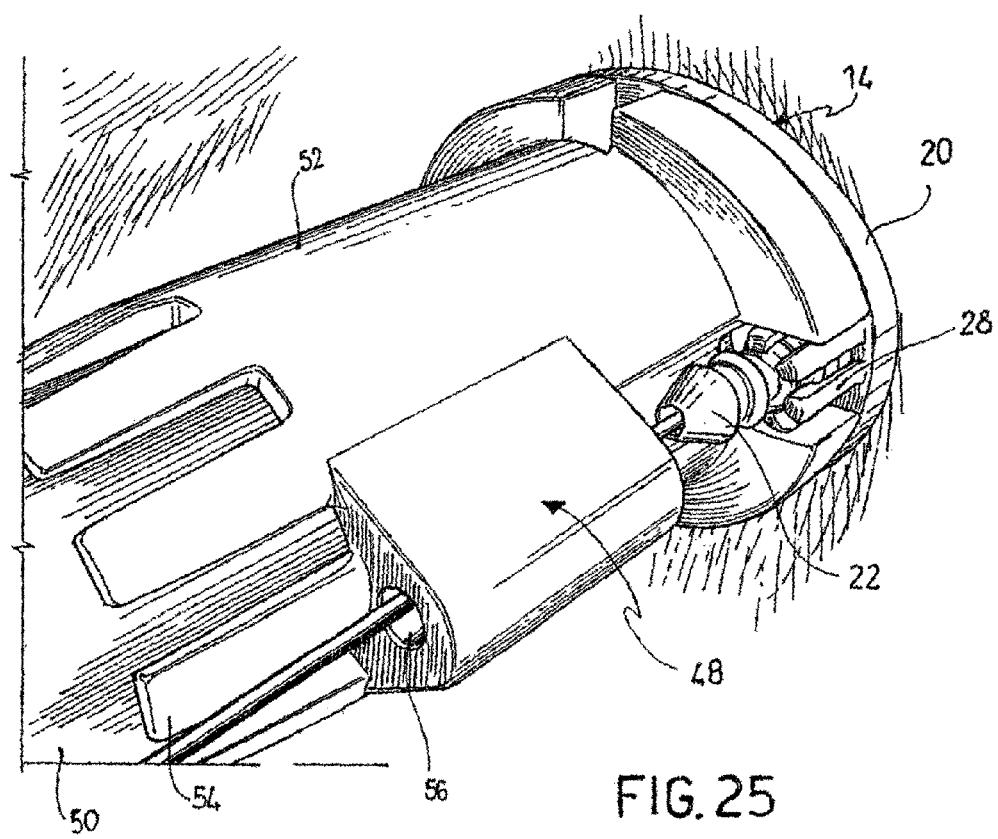
FIG. 25 illustrates a perspective view and from the interior of the stomach of a further step of the method.
Figure 26:
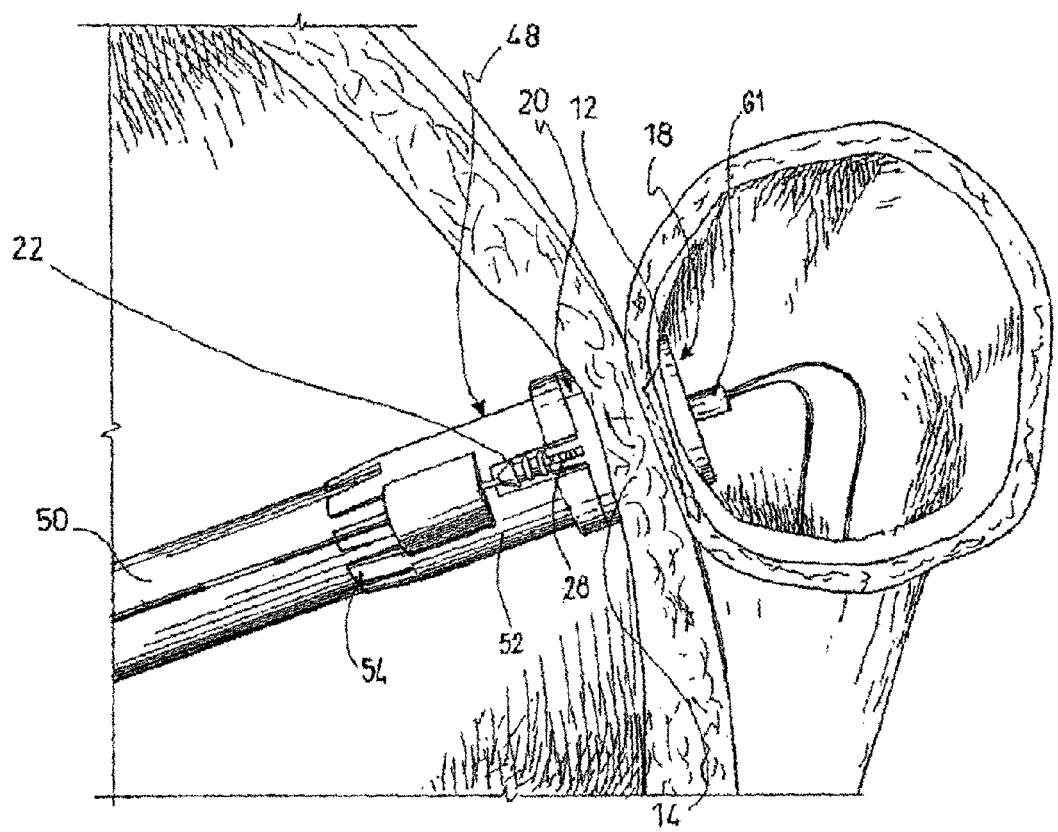
FIG. 26 illustrates the view from FIG. 25 according to a different point of view.
Figure 27:
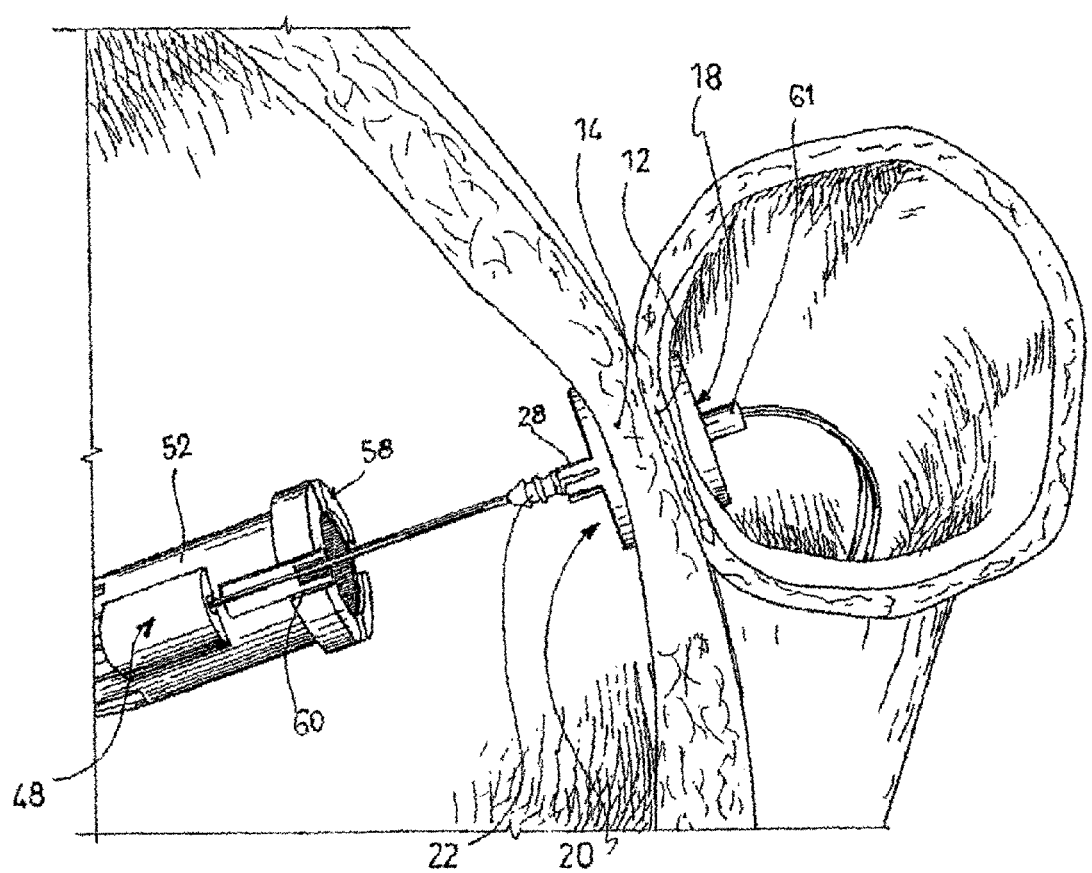
FIG. 27 illustrates a perspective view and from the interior of the stomach of a further step of the method.
Figure 28:
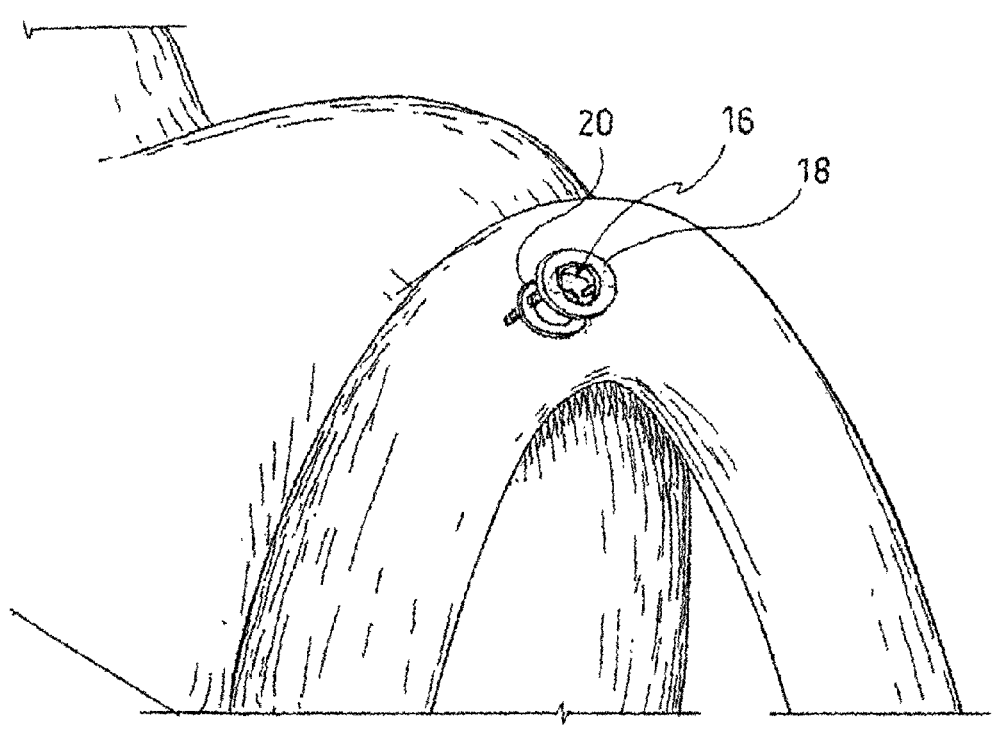
FIG. 28 illustrates a perspective, enlarged and partially phantom view of a detail of the portion of FIG. 1 at the end of a third sequence of steps of the method.
Figure 29:
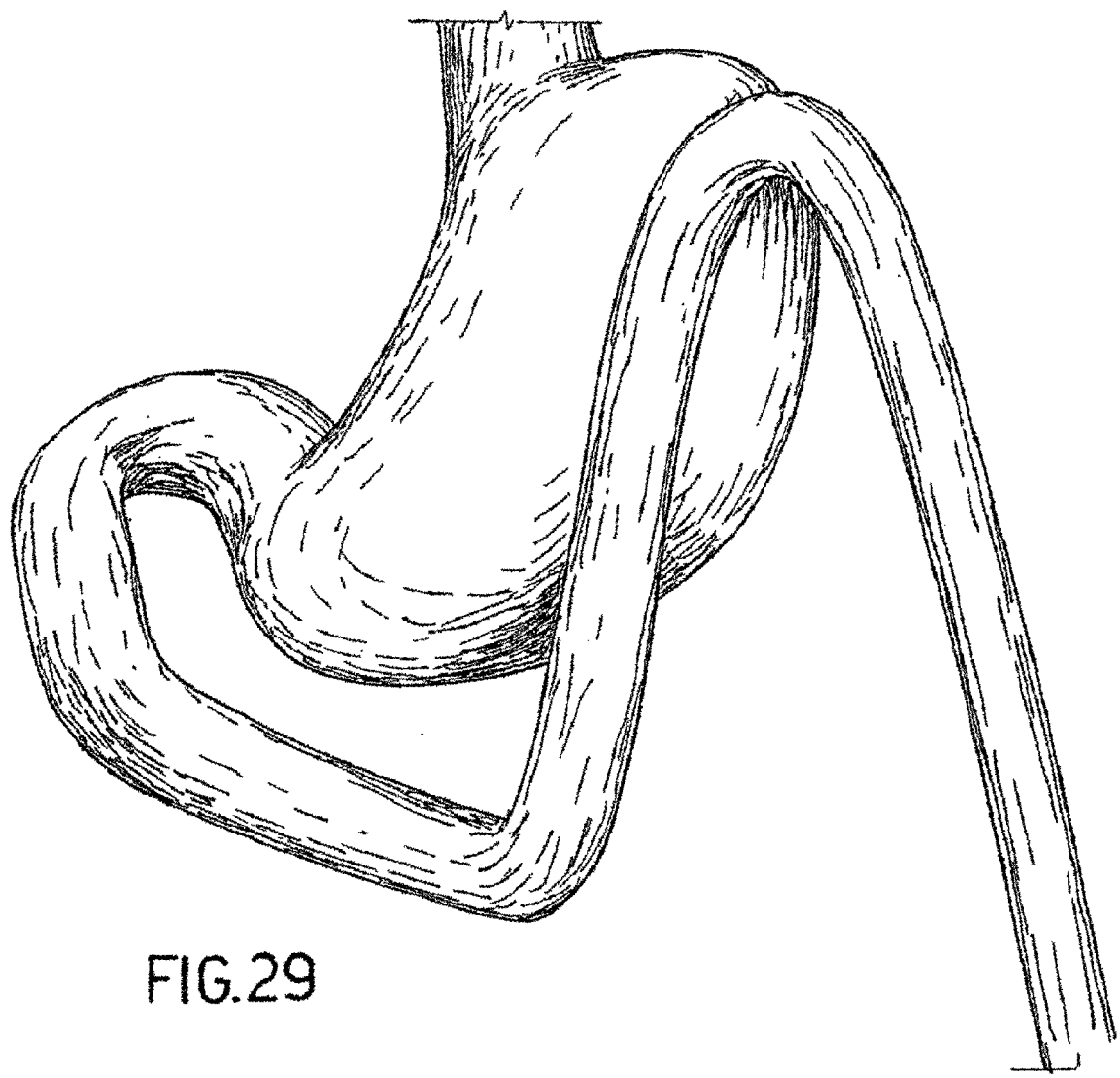
FIG. 29 illustrates a perspective view of the portion of FIG. 1 at the end of the third sequence of steps of the method.

By keeping to bias the elongated structure 50 along the guide wires, the pins 22 fit in the housings 24 of the locking portion and the frusto-conical end 32 enlarges the elastic tabs 28, which abut between a ring rib 30 and the next one, thus carrying out a snap fit (FIGS. 25 and 26). The bias exerted on the locking portion 20 via the head 52 and the elongated structure 50 allows selecting one of the possible mutual positions of the abutment portion 18 and the locking portion 20. In other terms, the presence of ring ribs 30 allows to define at least two relative positions between the abutment portion 28 and the locking portion 20, in order to establish an optimum compression degree of the tissues, which can be assessed as a function of their more or less ischemic coloration.

By withdrawing the positioning device 48, the locking portion 20 remains attached to the abutment portion 18 allowing to keep the two tissue portions (FIGS. 27 and 28) joined to each other. Subsequently, the anastomosis can be completed as will be described below.

The advantageous provision of an anastomotic device according to the above described aspects allows to provide an efficient and easily usable tool, and moreover a tool suitable for performing endoluminally anastomoses of tracts of the digestive tube, even if its use is possible also in other techniques, for example partially or wholly laparoscopic techniques or conventional surgical techniques.

A first object of the device is to provide an abutment portion which allows two tissue portions to be approximated, which are to be connected by anastomosis. According to this aspect, the advantageous provision of being able to be connected, or even locked, on at least two guide wires, allows to control and direct the anastomotic device throughout the path within the apparatus, both to approximate and connect the two tissue portions.

By providing an annular conformation which connects on two opposite sides two guide wires, it is possible to perform the anastomosis within the anastomotic device used in order to draw the tissues together. A possible completion step of the anastomosis will be described below.

A further advantage is given by the presence of two portions suitable for being connected or coupled to each other in such a way that the same device can be used both to approximate the two tissue portions and to keep the two tissue portions approximated. The locking is easy and effective, because it is done in a snap manner, furthermore with the possibility to determine different compression degrees of the tissues.

The latter aspect may be independent of the presence of one or more guide wires, even if the combination of the two aspects allows to accurately control and direct also the locking step, in particular in the case where the guide wires pass through the pins and the connecting housings between le two portions. As a consequence, it is further achieved a very compact anastomotic device.

According to a further aspect, the present invention relates to a kit comprising, in addition to the anastomotic device, also a positioning device 48 to deploy at least one portion of an anastomotic device 10 suitable for bringing and optionally to keep a first tissue portion 12 and a second tissue portion 14 approximated, which are intended to form an anastomosis.

According to a possible embodiment, the positioning device is suitable for deploying a locking portion 20 of an anastomotic device 10, for example as described above.

Furthermore, the positioning device is suitable for exert a bias on the locking portion 20 in order to snap fit the latter to an abutment portion 18 of the anastomotic device 10 oppositely located to the first and second tissue portion.

A positioning device according to the present invention, preferably suitable for sliding along a guide means, comprising at least one guide wire, has been described above. In particular, the positioning device comprises an elongated structure 50. In the examples as illustrated herein, the elongated structure 50 consists of a visualization device, for example of the gastroscope type.

According to a possible embodiment, particularly advantageous in the case of the visualization device, the positioning device comprises a head 52 suitable for interference fitting on a distal end of the visualization device 50. The head 52 is suitable for the abutment against a portion of the anastomotic device. Advantageously, the head comprises elastic tabs 54 which extend from a proximal end of the same head. Furthermore, the head 52 comprises at least one channel, preferably two channels 56 suitable for receiving a guide wire, respectively, such that the aforesaid positioning device is advantageously suitable for sliding along said guide means.

Advantageously, the head 52 comprises a distal end defining a thrust surface for the anastomotic device portion. In the case where the anastomotic device portion comprises housings suitable for receiving guide wires, the distal end of the head 52 comprises openings 60 to receive these housings.

According to possible variations to what has been illustrated, the positioning device can be slidable also on a single guide wire, by providing for example a channel 56 of the head 52.

In accordance with possible variations to what has been illustrated herein, the head 52 can be applied to any type of elongated structure.

The positioning device allows to adapt already existing structures, such as visualization devices (gastroscopes), in particular with the aim to carry out an endoluminal technique to perform anastomoses of tracts of the digestive tube.

The elongated structure can however be done both via a flexible structure, and via a rigid structure, in order to exert a higher bias on the anastomotic device, and via a "stiffening" structure, i.e. a flexible structure suitable for becoming rigid.

An application and operation example of the positioning device 48 has been described above with reference to FIGS. 22-28.

The positioning device according to the present invention is easy and efficient and, by being able to slide on guide wires, it allows for a correct positioning of the two portions of the anastomotic device.

A method for performing anastomoses in tracts of the digestive tube in which an anastomotic device 10 is used according to one of the above aspects is described below. Referring to annexed Figures, a method for performing a gastro-jejuno anastomosis in which an anastomotic device 10 is used according to one of the above aspects has been illustrated. Of course, further and different uses are possible, for example in a method for performing generally entero-entero anastomosis or, more particularly, jejuno-jejuno anastomosis or ileo-jejuno anastomosis.

A first step of the aforesaid method provides for the introduction, through a natural orifice or other luminal structures, of at least two guide wires A and B placed beside one to the other, for example essentially parallel. The guide wires extend between proximal end portions A' and B' and distal end portions A" and B" and pass through a first tissue portion 12 and a second tissue portion 14 where the anastomosis is to be performed.

In accordance with what has been illustrated, the guide wires are spaced apart one from the other both in the introduction step and in the passing-through step of the first tissue portion to be connected by anastomosis. According to an alternative embodiment, the guide wires are approximated and placed beside one to the other also in the introduction and the passing-through step of the first tissue portion. In the latter case, they can also be connected at the distal end to be subsequently separated when the insertion has been completed.

The aforesaid method provides the insertion of an anastomotic device along the two guide wires by locking it in a direction and dragging it to the anastomotic site, by drawing the first tissue portion and the second tissue portion together and performing an anastomosis. The anastomotic device can be pre-assembled on the guide wires, or it can be locked on the guide wires already shaped in a loop.

In particular, the two guide wires are located so as to form a loop with the end portions at natural orifices, or other orifices, while the loop passes through the first tissue portion 12 and the second tissue portion 14 to be connected. The anastomotic device is inserted along the two loop-shaped wires to perform the anastomosis endoluminally.

In order to form the loop, the distal ends of the two guide wires are first inserted to the first tissue portion 12 and introduced through it until passing it through and to project oppositely. Preferably, the two guide wires are inserted through an insertion device 62 at least until reaching and passing through the first tissue portion 12.

Figure 31:
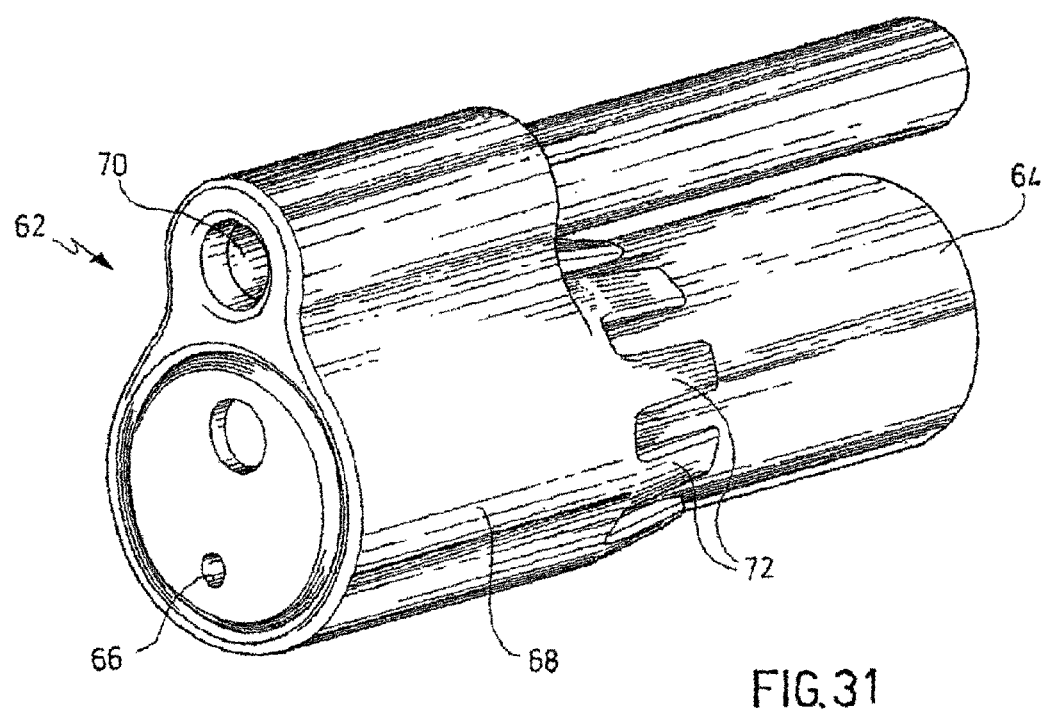
FIG. 31 illustrates a perspective and enlarged view of a detail of an insertion device suitable for being used in some steps of the method.
Figure 32:
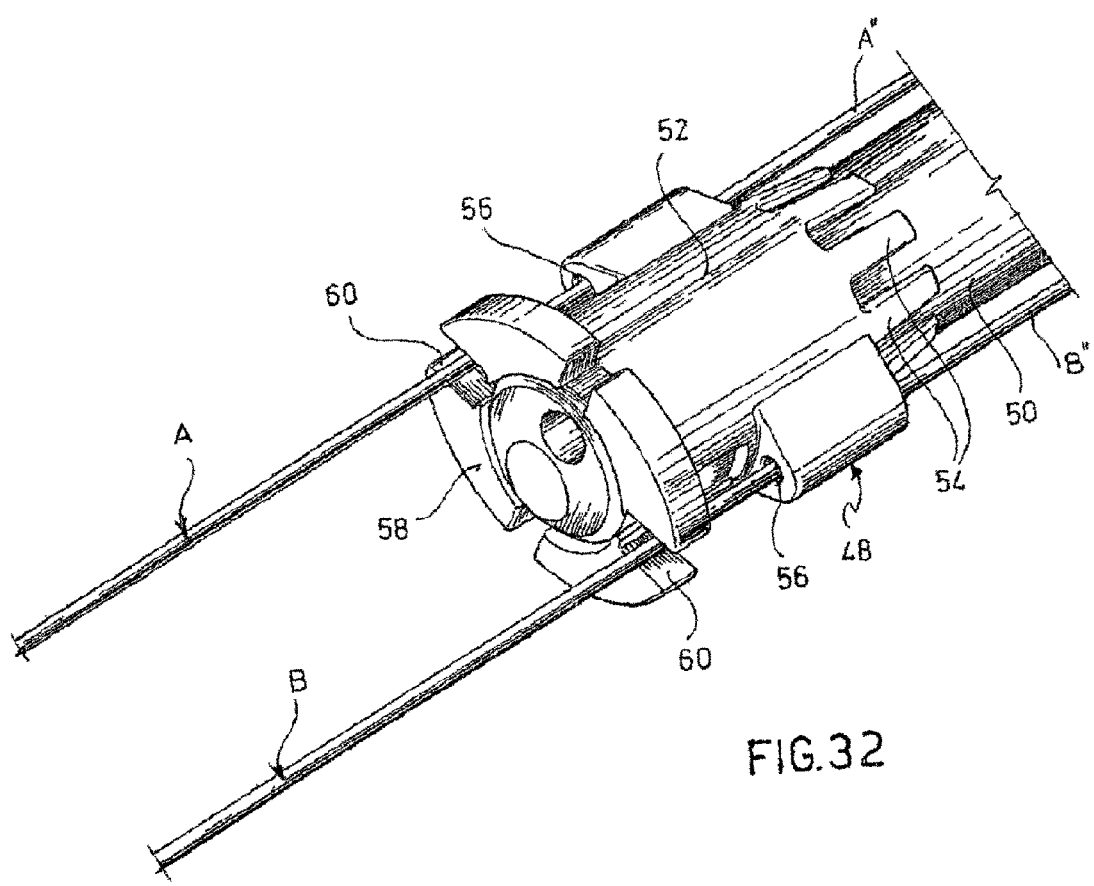
FIG. 32 illustrates a perspective view of a positioning device according to the present invention suitable for being used in some steps of the method.

Referring to the FIG. 31, the insertion device 62 comprises an elongated structure that is preferably obtained by means of a visualization device, for example, a gastroscope 64, provided with a first operative channel 66 suitable for receiving and inserting one of the guide wires. Advantageously, a connecting head 68 suitable for being mounted to a distal end of the elongated structure (visualization device 64) can be further provided. The connecting head 68 is integral with at least one second operative channel 70 suitable for receiving and inserting another guide wire of said guide wires. The operative channel 70 extends essentially throughout the length of the elongated structure to keep the two guide wires distinct during the insertion. Advantageously, the second operative channel 70 is located externally to the elongated structure, made integral with the latter by the connecting head 68.

In particular, the first and second operative channels are suitable for deploying respectively a guide wire in a method for performing anastomoses in tracts of the digestive tube.

Advantageously, the operative channels are located at a determined distance one from the other, so as to keep the guide wires apart during the insertion and the passing through of the first tissue portion. Preferably, the second operative channel 70 is located oppositely of the visualization device 64 with respect to the first operative channel 66.

In accordance with a possible embodiment, the connecting head 68 of the insertion device 62 is suitable for an interference fitting on a distal end of the elongated structure (visualization device 64). For example, the connecting head 68 comprises elastic tabs 72 which extend from a proximal end of the head.

In accordance with an alternative embodiment, the insertion device has a single operative channel in order to insert the guide wires simultaneously and placed beside one to the other. In this case, the guide wires pass through the first tissue portion through the same opening. Optionally, the two guide wires can be originally connected one to the other at the distal end and, subsequently, separated at the end of their insertion.

Figure 2:
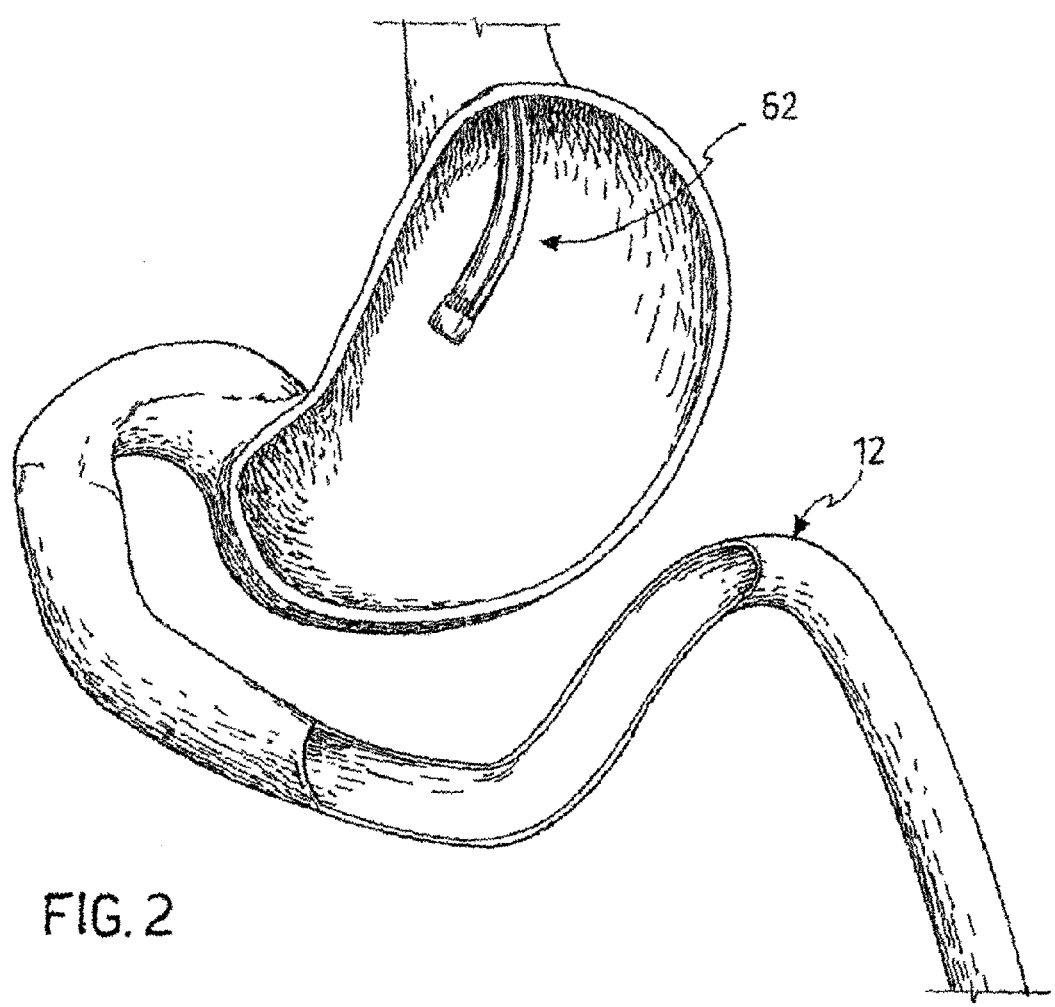
FIG. 2 illustrates a step of a method for performing anastomoses in tracts of the digestive tube carried out on the portion of FIG. 1.
Figure 3:
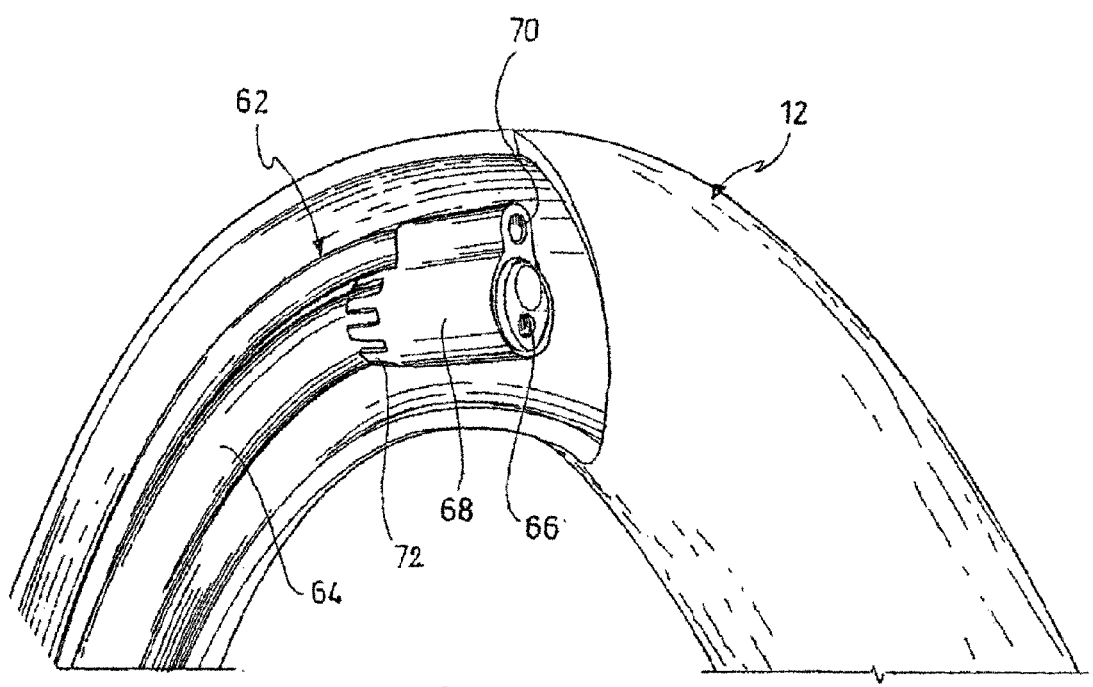
FIGS. 3 to 6 illustrate perspective and enlarged views of a detail from FIG. 1 corresponding to further steps of the method, respectively.

The insertion device 62 is assembled externally to the patient, inserting the connecting head 68 on the distal end of the elongated structure (visualization device 64—FIG. 31). Subsequently, the insertion device 62 is introduced in the oesophagus and in the stomach (FIG. 2) to the jejune and the first tissue portion 12 (FIG. 3).

Figure 4:
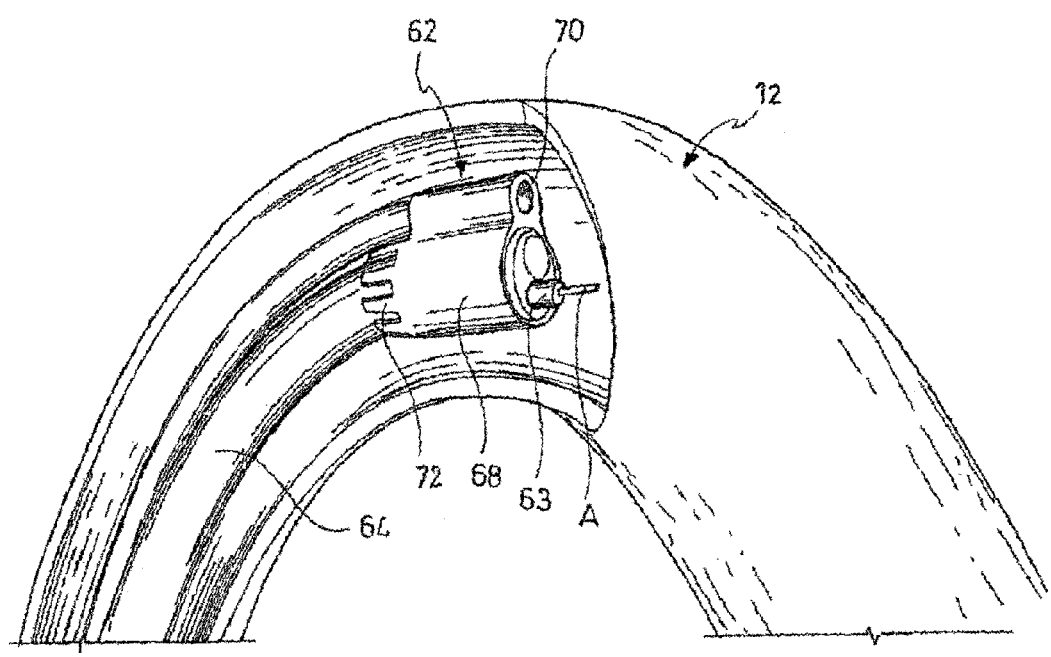

A guide wire A is inserted through the first operative channel 66 until a distal end of the guide wire projects from the distal end of the insertion device 62 (FIG. 4) and passes through the wall of the first tissue portion. A distal end portion A" of the guide wire extends beyond the wall of the first tissue portion.

Figure 5:
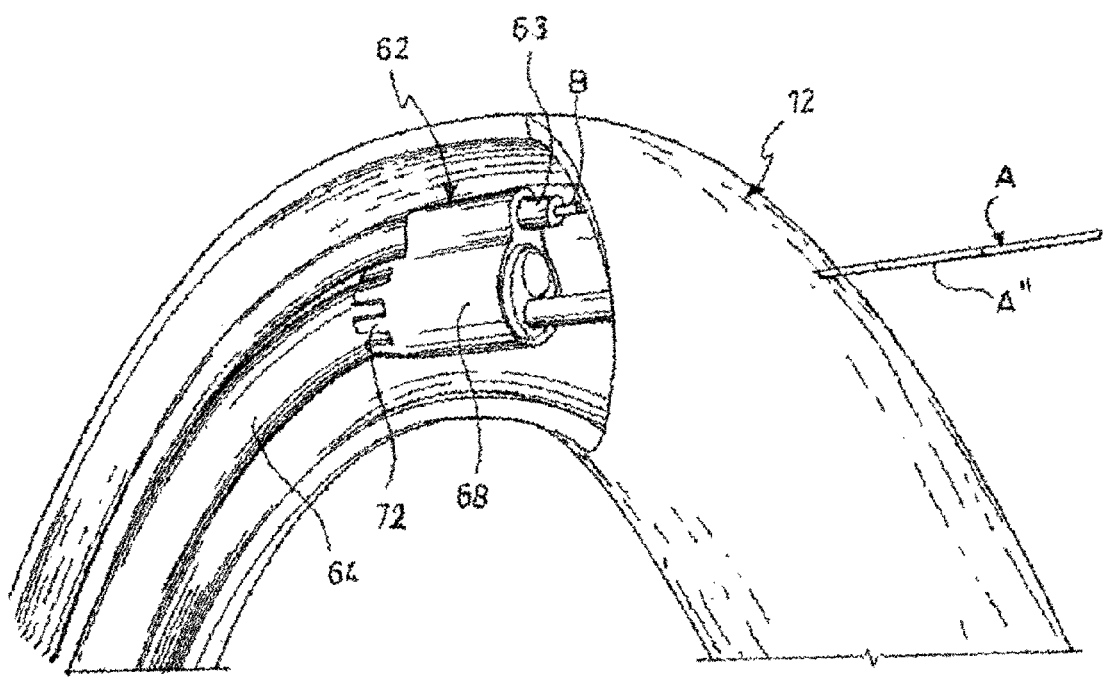
Figure 6:
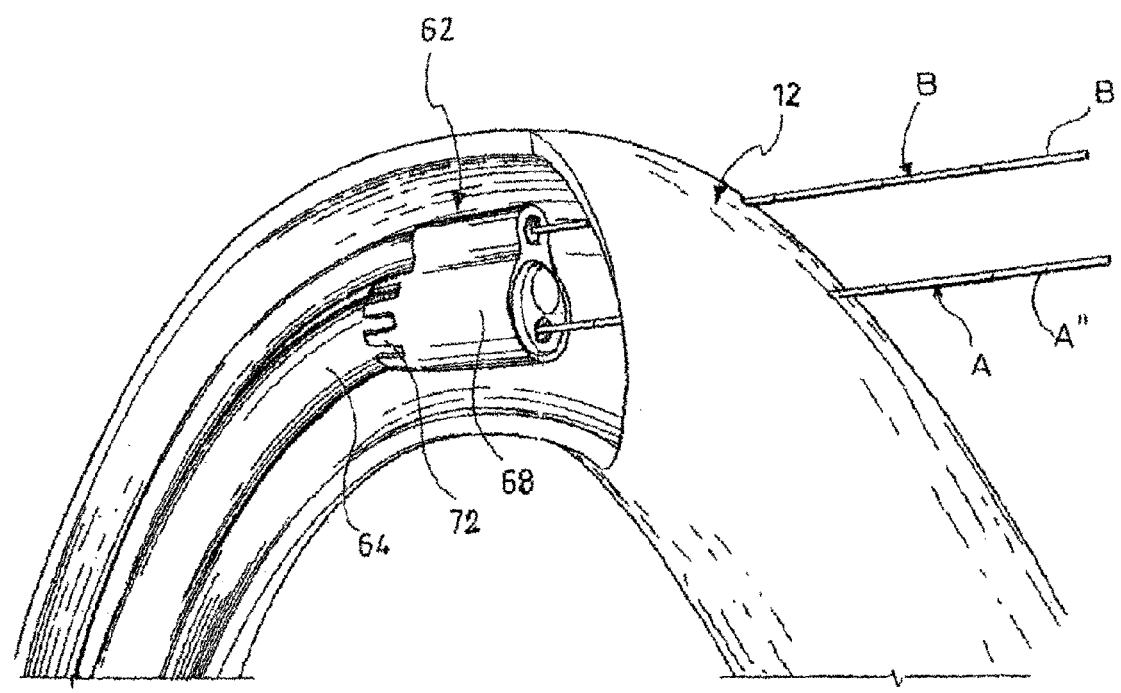
Figure 7:
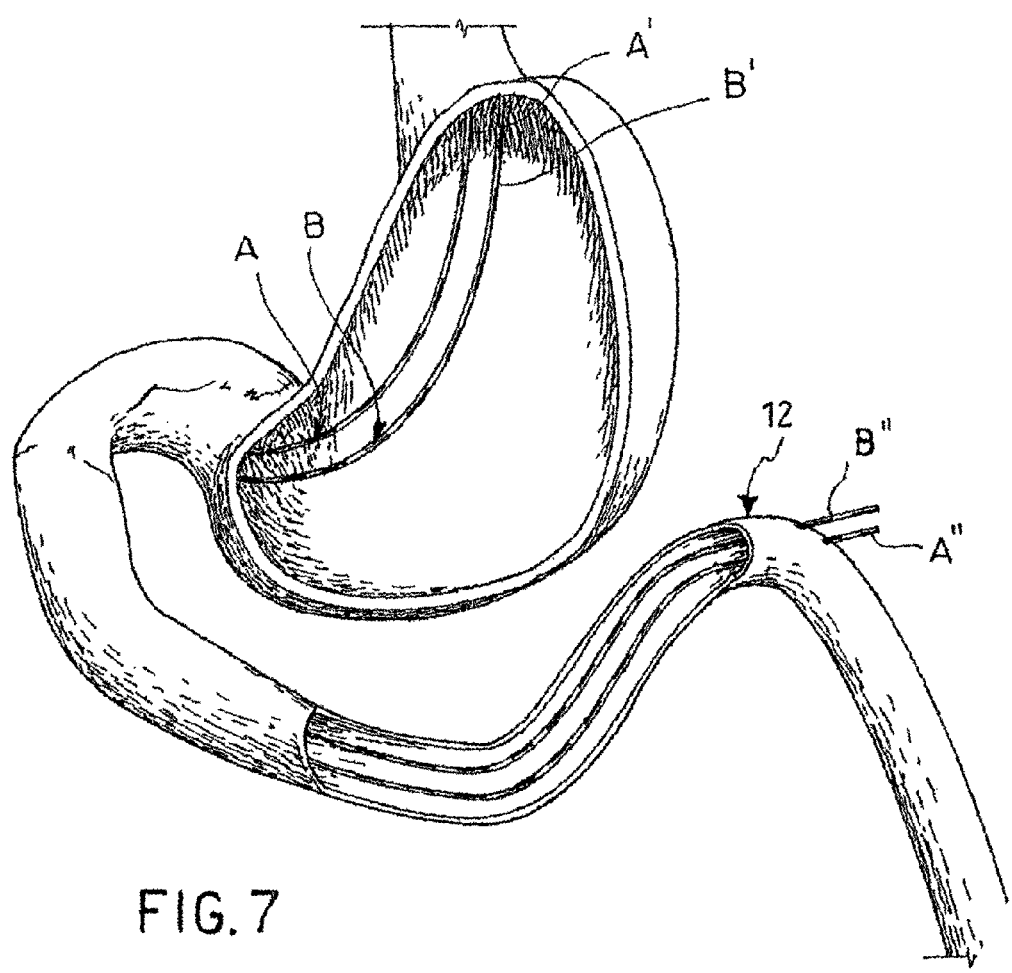
FIG. 7 illustrates the perspective and partially sectional view of FIG. 1 at the end of a first sequence of steps.

Furthermore, a second guide wire is inserted through the second operative channel 70 until a distal end of the guide wire projects from the distal end of the insertion device 62 (FIG. 5) and passes through the wall of the first tissue portion. A distal end portion B" of the second guide wire extends beyond the wall of the first tissue portion (FIG. 6). The insertion device is then retracted (FIG. 7).

Before introducing the guide wires, the first tissue portion wall is punched for example by means of radiofrequency or via other devices, optionally introduced by means of the same insertion device 62. For example, a sheath 63 containing a radiofrequency needle is inserted along the first operative channel 66 until the first tissue portion wall. The radiofrequency needle punches the wall, and subsequently a guide wire A is inserted along the sheath until passing through the first tissue portion wall, at the hole punched by the radiofrequency needle. The same procedure can be followed in the guide wire B positioning through the second operative channel 70. In this case, to each guide wire corresponds an opening through the first tissue portion and the guide wires are at least partially spaced apart from each other. In the case illustrated in the Figures, the first tissue portion essentially corresponds to a jejune tract, and the guide wires pass through it, provided the performing of a jejunostomy.

In accordance with a different embodiment and application example, the guide wires are inserted approximated and placed beside one to the other through a single operative channel, for example of an insertion device or of a visualization device. Before introducing the guide wires, the first tissue portion wall is punched in a single point, for example by means of radiofrequency or through other devices, optionally introduced by means of the same insertion device. The distal end portions of the guide wires can be connected, at least during the introduction step.

Figure 8:
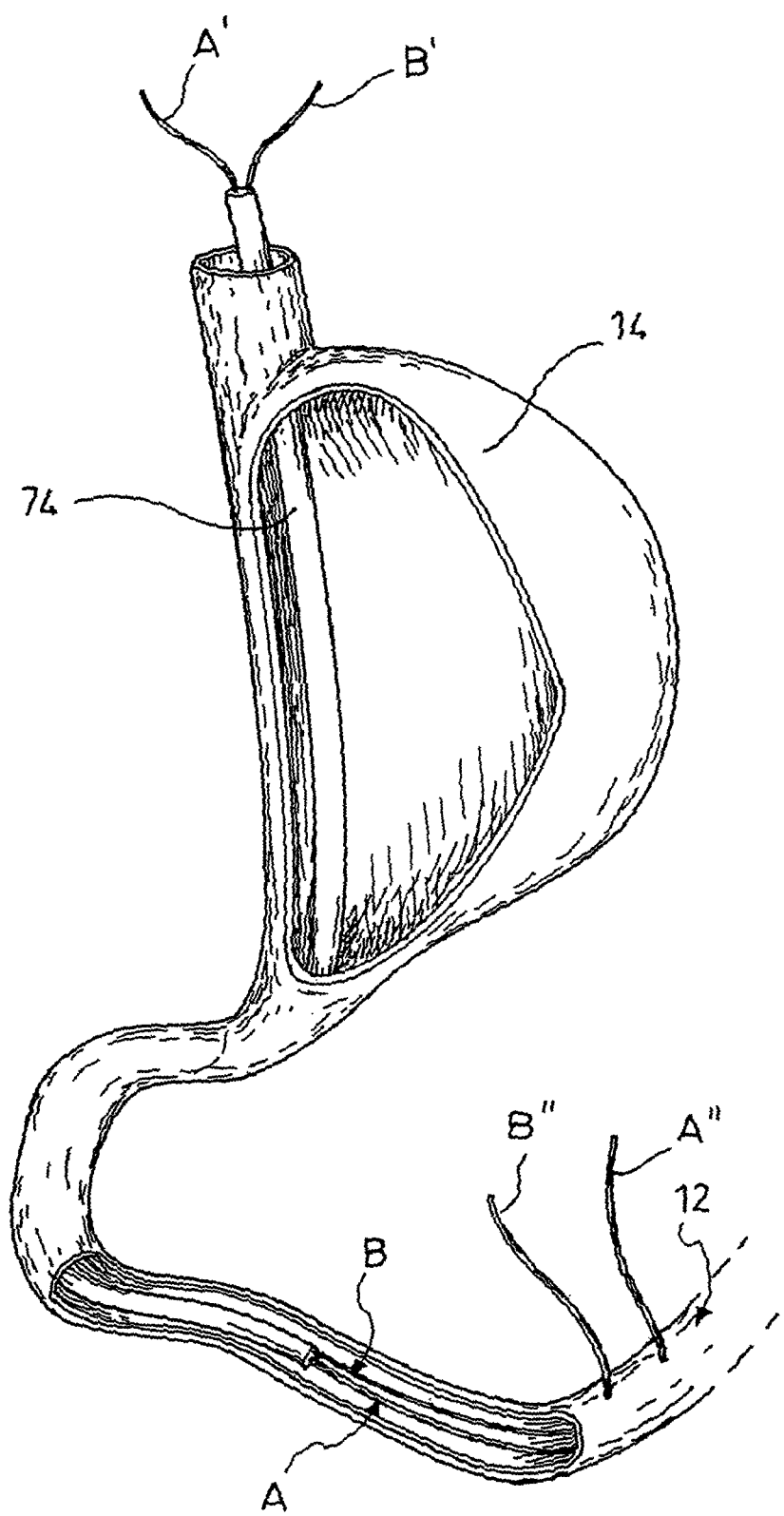
FIG. 8 illustrates the perspective and partially sectional view of FIG. 7 according to a possible variation of the method.
Figure 9:
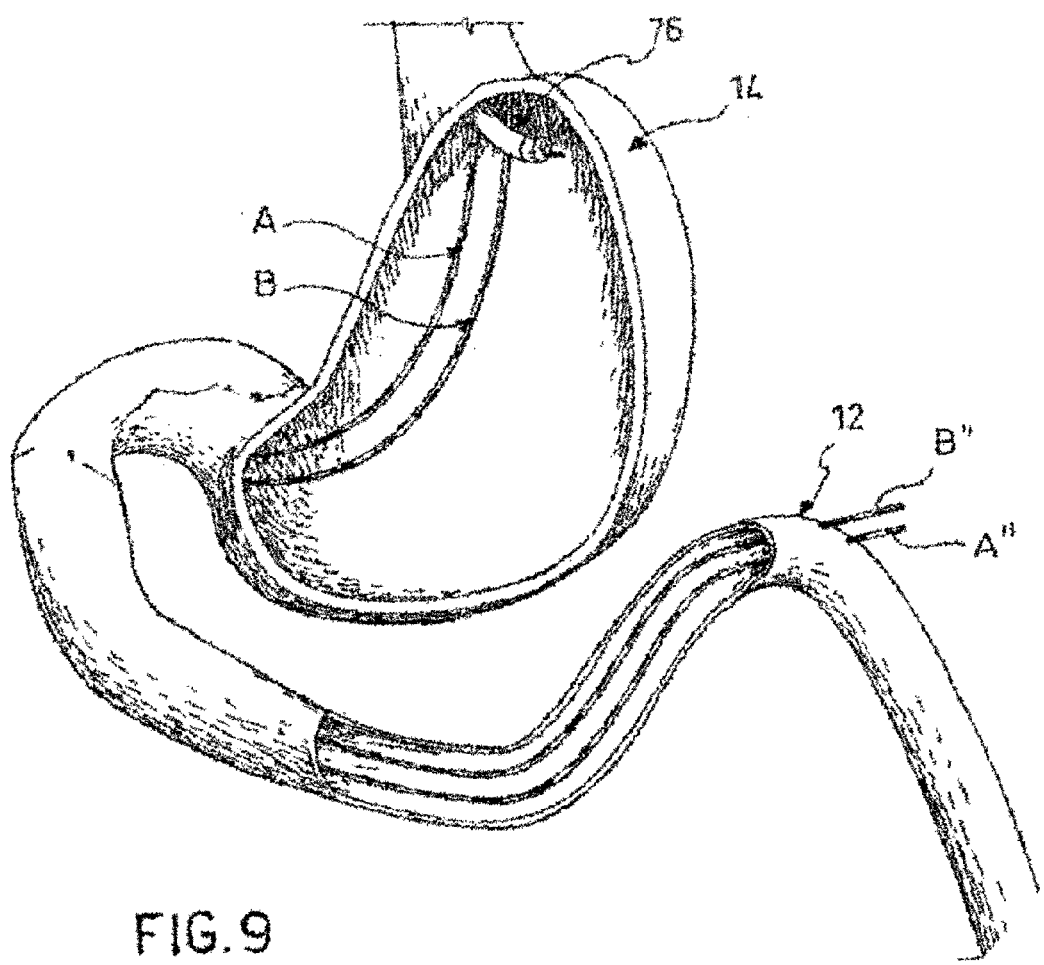
FIG. 9 illustrates a further step of the method carried out on the portion of FIG. 7.

Optionally, preferably before passing through the second tissue portion, a separation and identificative step of the proximal end portions A' and B' of the guide wires which come out of the luminal structure is provided. Preferably, the separation and identificative step of the proximal end portions of the guide wires which come out of the luminal structure is performed introducing a first sheath 74 on the two guide wires starting from a proximal end of the same guide wires. The first sheath has a characterizing element, for example it is made in a prefixed colour (FIG. 8).

Figure 10:
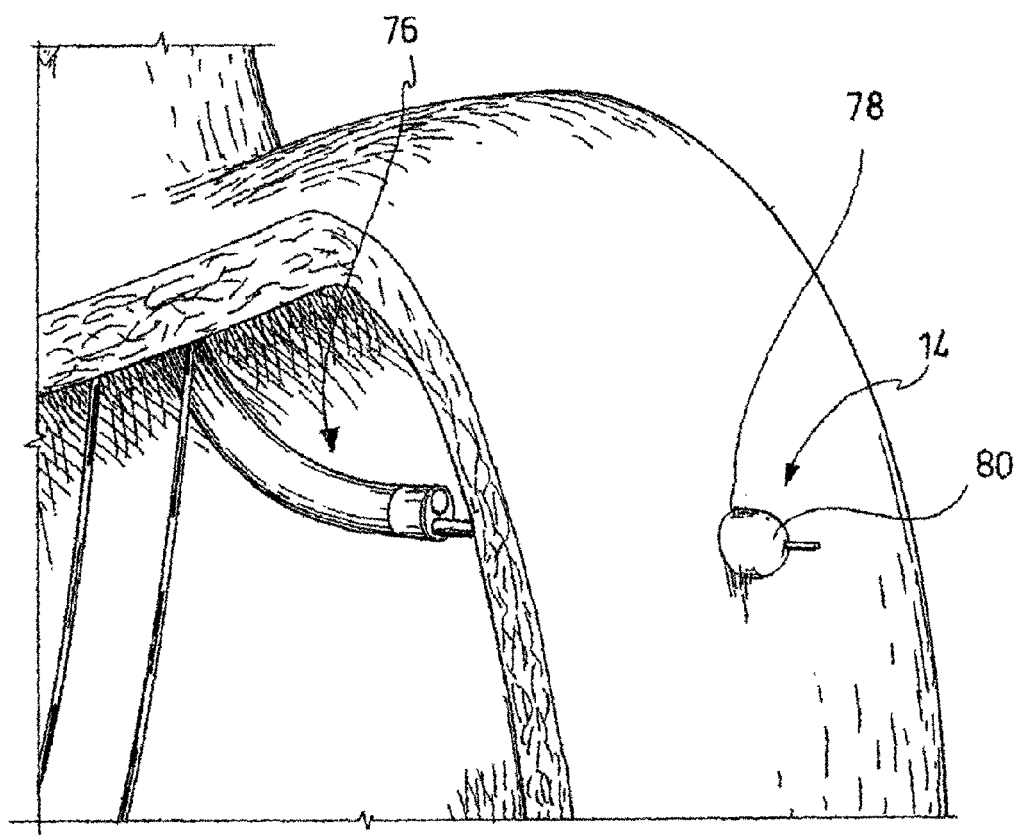
FIGS. 10 and 11 illustrate perspective and enlarged views of a detail from FIG. 7 corresponding to further steps of the method, respectively.
Figure 11:
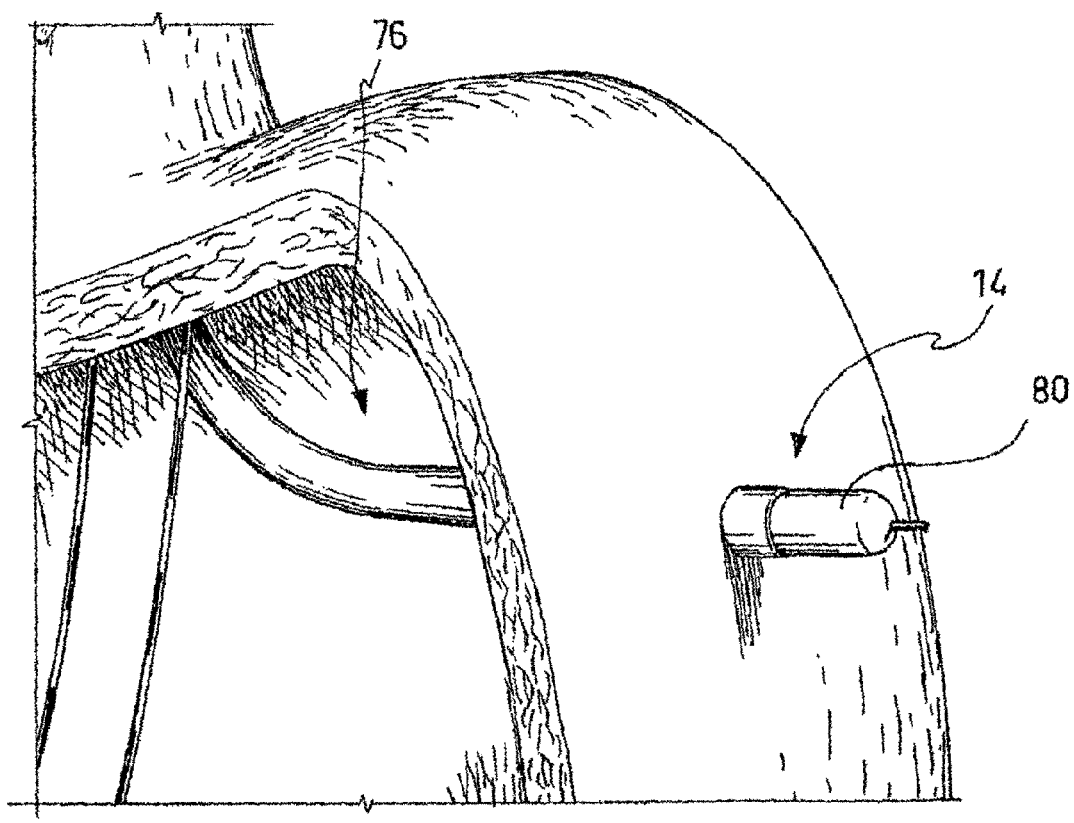

To complete the loop, the insertion of a grasping device 76 through the second tissue portion 14 to be connected to grasp the distal end portions A" and B" of the two guide wires is advantageously provided. In order to make the grasping device pass through the second tissue portion, the creation of a hole 78 (gastrostomy with reference to Figs.) in the second tissue portion 14, for example by a radiofrequency needle or other is advantageously provided. The hole 78 is optionally enlarged by a balloon catheter 80, preferably introduced via an operative channel of the grasping device (FIGS. 10 and 11).

Figure 12:
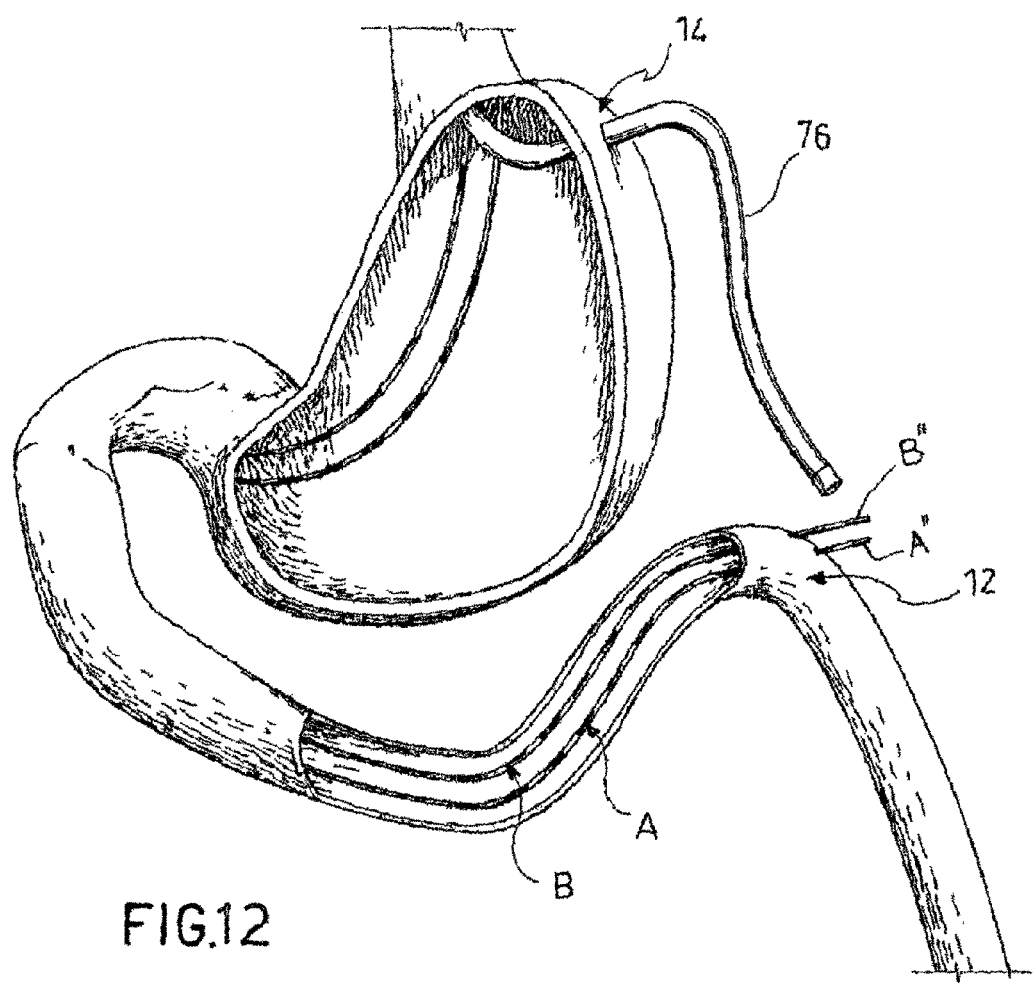
FIG. 12 illustrates a further step of the method carried out on the portion of FIG. 7.
Figure 13:
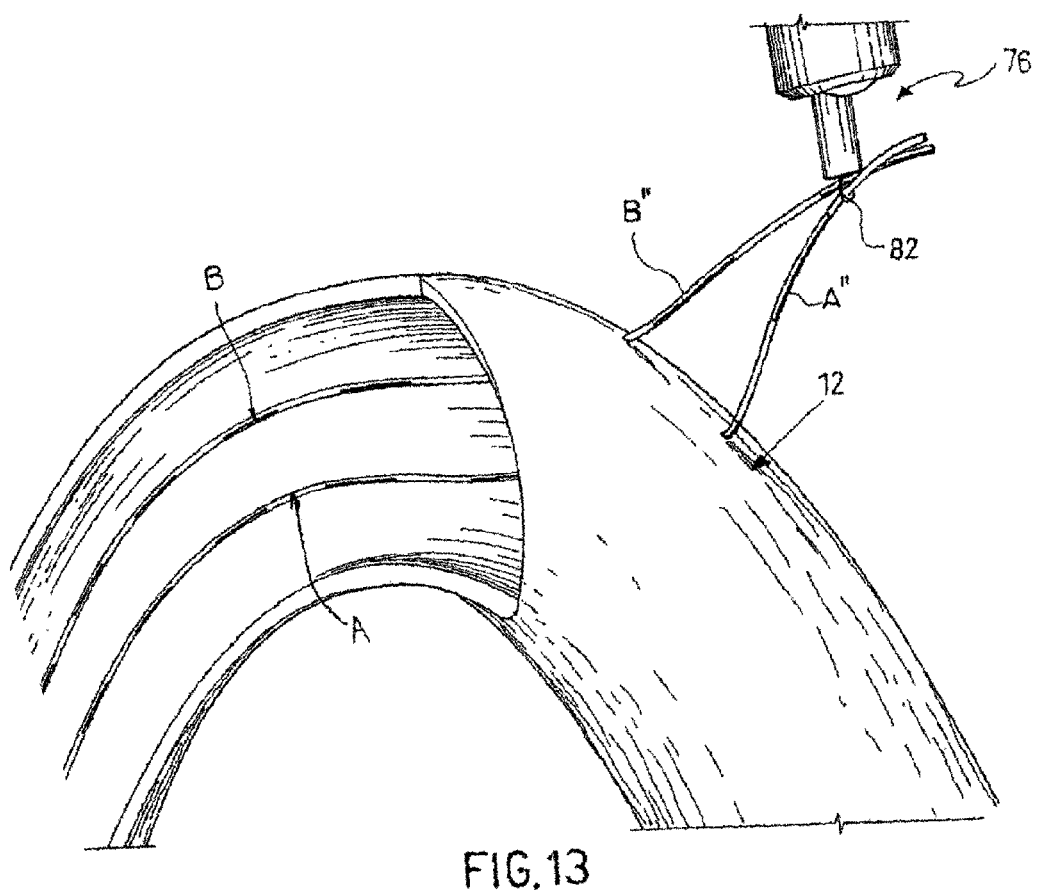
FIG. 13 illustrates a perspective and enlarged view of a detail from FIG. 12 corresponding to a further step of the method.
Figure 14:
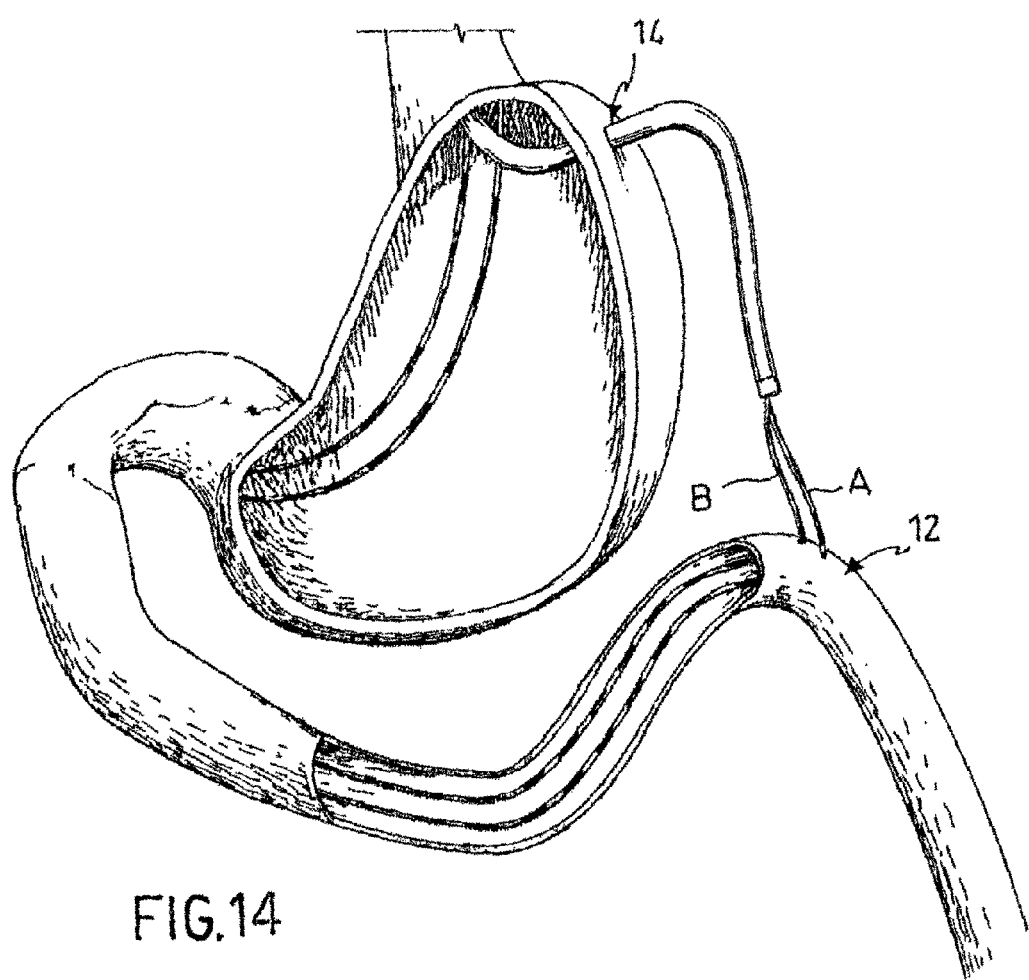
FIG. 14 illustrates a further step of the method carried out on the portion of FIG. 7.
Figure 15:
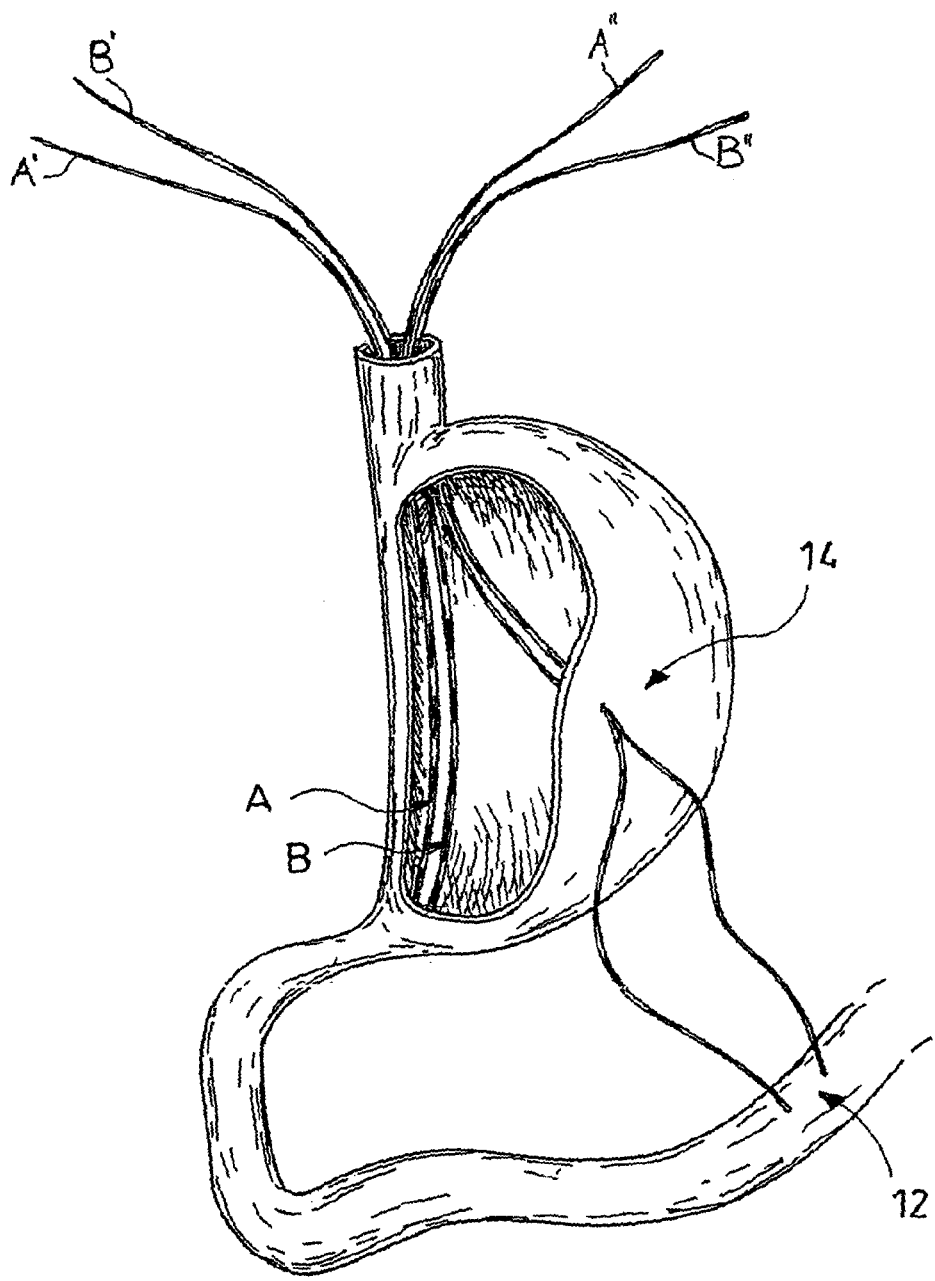
FIG. 15 illustrates the perspective and partially sectional view of FIG. 7 at the end of a second sequence of steps of the method.

In accordance with a possible embodiment, the grasping device comprises a visualization device, for example of the gastroscope kind, in which an operative channel is used to insert the balloon catheter 80 and subsequently a snare 82 for grasping the distal end portions A" and B" of the guide wires. The grasping device 76 passes through the hole 78 and reaches the distal ends of the guide wires (FIG. 12). When the snare closes on the distal end portions of the guide wires (FIG. 13), the snare, together with the grasping device, is retracted through the hole 78 (FIG. 14) to the orifice through which it had been introduced. The guide wires are then located to form a loop with distal and proximal end portions preferably brought back in the same orifice (FIG. 15).

The grasping device can be activated in a wholly endoluminal way, or through laparoscopic supervision. According to this alternative, not shown, the hole 78 (gastrostomy) is not enlarged and only the loop is made to pass through it. Subsequently, the surgeon laparoscopically individuates the distal end portions A" and B" and inserts them into the loop, under laparoscopic control. Finally, the loop is closed again and dragged back so as to form the loop, as provided in FIG. 15.

Figure 16:
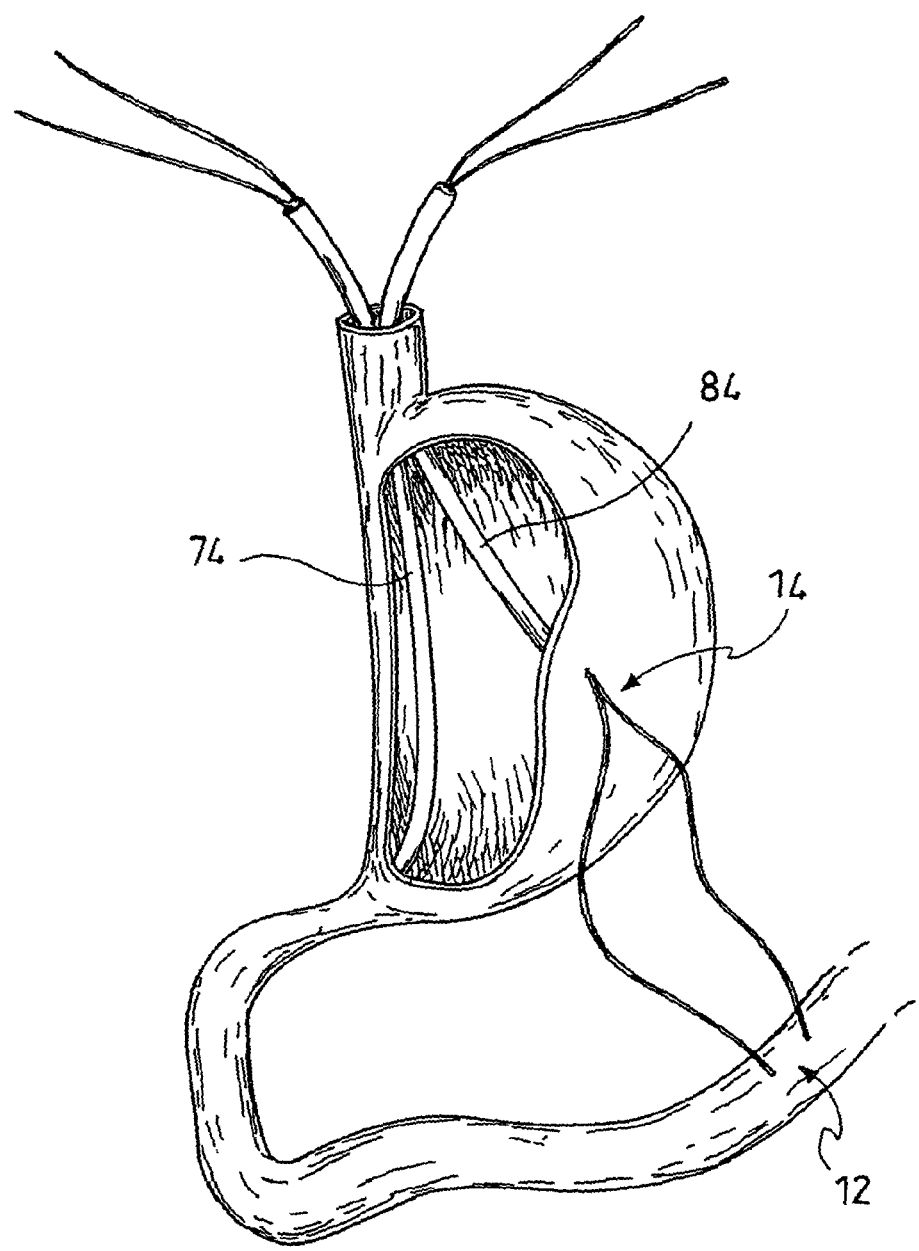
FIG. 16 illustrates the perspective and partially sectional view of FIG. 8 according to a possible variation of the method.

Optionally, a separation and identificative step is provided on the distal end portions of the guide wires that come out of the luminal structure after they have passed through the first and second tissue portions. Advantageously, this separation and identificative step on the distal end portions of the guide wires is performed by introducing a second sheath 84 on the two guide wires starting from the distal end of the same guide wires. The second sheath presents a characterizing feature, for example a colour different from that of the first sheath 74 (FIG. 16).

Once the loop has been formed, the anastomotic device is inserted on the two guide wires so as to approximate and optionally keep the first tissue portion and the second tissue portion together, as described above. Optionally, the abutment portion 18 is pre-associated or integral to the guide wires in such a way that when the distal ends of the guide wires are dragged, the abutment portion is dragged and approximated to the tissue portions to be connected.

In the case where the distal end portions of the guide wires are connected, it is possible to divide them after forming the loop, or subsequently to the formation of the same.

In the case where the first sheath 74 is provided, the abutment portion 18 of the anastomotic device 10 is inserted on the proximal end portions of the guide wires after removing the first sheath 74 which, when the abutment portion of the anastomotic device has approximated the two tissue portions to be connected, is preferably repositioned on the proximal end portions of the guide wires.

In the case where a second sheath 84 is provided, the locking portion 20 of the anastomotic device 10 is subsequently inserted on the distal end portions A" and B" of the guide wires after removing the second sheath 84.

The final step of the method provides for the completing of the anastomosis. Using the anastomotic device as described above, the anastomosis is performed at the opening of the two annular structures of the anastomotic device.

Referring to the application described in the annexed Figures, according to a preferred embodiment the anastomosis is performed on the side of the jejune, introducing for example a radiofrequency needle suitable for punching the wall. Optionally, a balloon catheter is subsequently introduced to enlarge the punching and/or a further tool to remove part of the tissue. According to an alternative embodiment, the anastomosis can be performed on the side of the stomach. In this case it is possible to provide the introduction of a shielding device in the jejune, in order to avoid that the punching affects also the jejune wall opposite to that in which the anastomosis has to be performed.

Finally, the guide means (guide wires) are removed, for example by pulling the proximal end portions A' and B', as in the case where the locking members 61 are provided. In other terms, the guide wires are pulled in the direction in which they can slide with respect to the anastomotic device. Optionally, a seal test of the anastomosis based on methylene blue can be provided.

Figure 1:
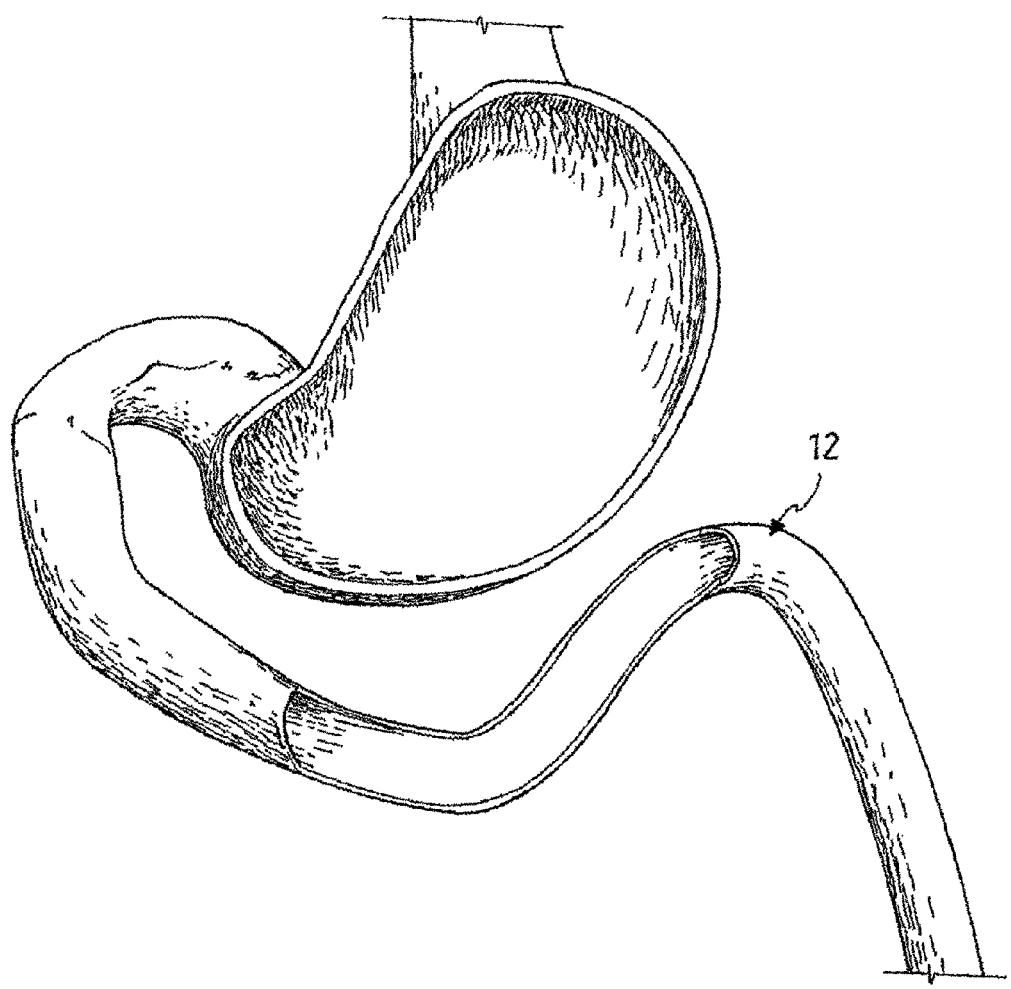
FIG. 1 illustrates a perspective view of a portion of stomach and intestine partially in section.

With reference to the annexed Figures, the aforesaid method can be used for example in a performing step of a gastro-jejuno anastomosis (G-J), advantageously endoluminally. In fact, FIG. 1 illustrates a portion of the digestive apparatus comprising the oesophagus, the stomach and a tract of the intestine corresponding to the jejune. The two guide wires A and B are introduced through the oesophagus, which represents a natural orifice, or through another orifice, also artificial, until reaching the stomach and a tract of the jejune (FIG. 7). Subsequently, the two guide wires A and B are loop-shaped with distal A", B" and proximal end portions A', B' debouching through the aforesaid orifice (FIG. 15). The loop passes through the portions to be connected, respectively a jejunostomy and a gastrostomy.

Particularly, the two guide wires A and B are introduced through the oesophagus, the stomach and a tract of the jejune and one distal end thereof is made to pass through the jejune wall corresponding to the first tissue portion to be connected (FIG. 6), for example after punching this wall through radiofrequency needles as described above. This step is performed preferably via an insertion device 62 as illustrated in FIGS. 2-6, as described above. According to a different embodiment and application example, the guide wires are inserted approximated and placed beside one to the other through a single operative channel, for example of an insertion device or of a visualization device. Before introducing the guide wires, the first tissue portion wall is punched in a single point, for example by means of radiofrequency or through other devices, optionally introduced by the same insertion device.

In the case where the aforesaid method is a part of a gastro-intestinal by-pass procedure, it will be possible to subsequently proceed to the performing of a further entero-entero anastomosis (for example a jejuno-jejuno or an ileum-jejuno anastomosis), optionally by repeating the steps previously described.

The method can be optionally performed also using a single guide wire when using an anastomotic device suitable to the purpose.

Such as described in the broadest embodiment thereof, or in the specific application to perform a gastro-jejuno anastomosis (G-J), the aforesaid method allows a continuous control both in the positioning step of the guide wires and in the step of approximating and connecting the tissue portions. The provided steps further allow an endoluminal approach for procedures until now applied in the conventional surgery or laparoscopically, even if laparoscopic or partially laparoscopic techniques are not excluded.

The above described method can be further used to perform different kinds of anastomoses, for example a jejuno-jejuno anastomosis, in particular to achieve a gastro-intestinal by-pass, or a colon-colon anastomosis with transanal access.

Figure 35:
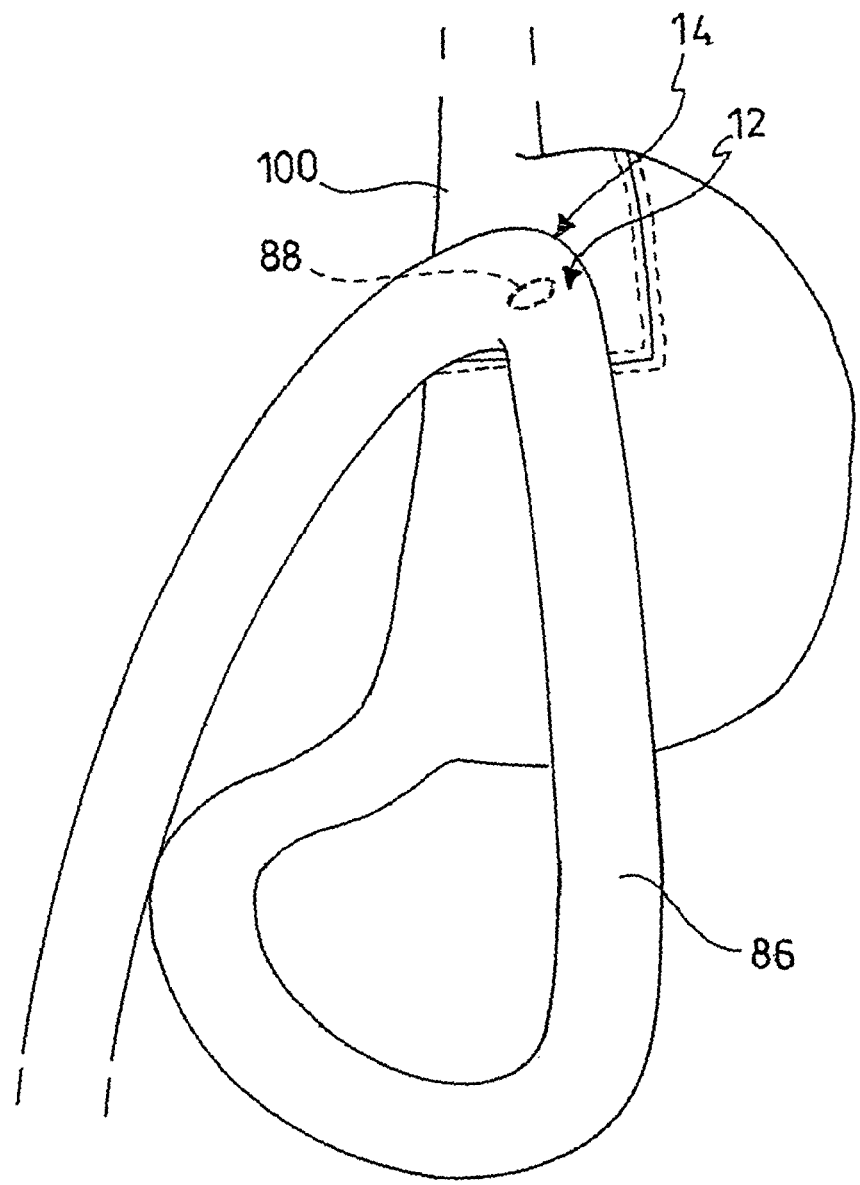
FIGS. 35 and 36 illustrate two corresponding steps of a possible embodiment of a method for performing anastomoses in tracts of the digestive tube.
Figure 36:
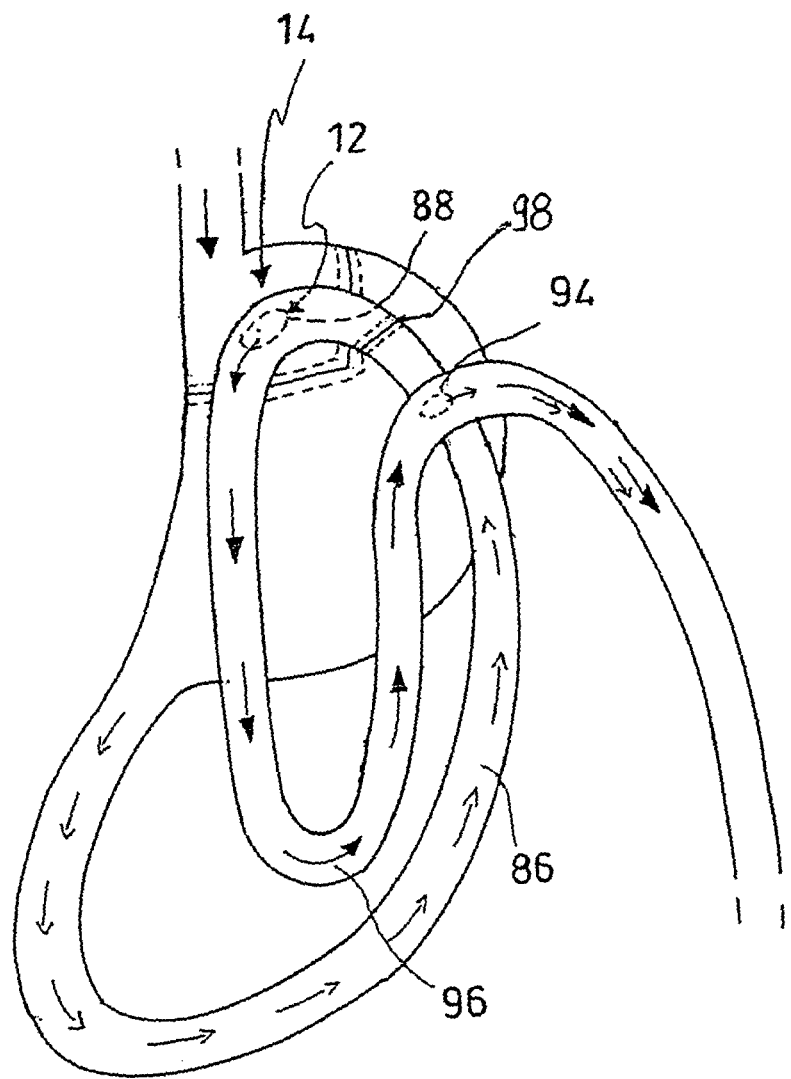

According to a possible embodiment, the aforesaid method to perform anastomoses in tracts of the digestive tube can be applied in the case illustrated in FIGS. 35 and 36, in particular to obtain a gastro-intestinal by-pass. This method comprises drawing-together and connection steps of the tissues 12, 14 to form anastomoses 88, 94 adapted to keep or to reintegrate the integrity and the continuity of the intestinal duct after each formation of an anastomosis (both the gastro-jejuno anastomosis and the jejuno-jejuno anastomosis). Furthermore, the gastro-jejuno anastomosis and the jejuno-jejuno anastomosis are performed at a closed-up distance, thus allowing for a wide operative and visual field, while staying only in the upper area of the abdomen.

In this case also, the steps of bringing tissues closer and to create the gastro-jejuno anastomosis and/or the jejuno-jejuno anastomosis can be performed using a guide means comprising preferably at least two guide wires placed beside one to the other and located to form a loop which passes through the tissue portions to be connected. The guide means can be associated to an anastomotic device according to the present invention or to other anastomotic or positioning devices. The aforesaid method can be performed endoluminally, or in a partially or wholly laparoscopic way.

In all the cases provided, the partial creation of a pocket 100 into the stomach, to which the first portion of the jejune will be connected, can be preventively provided.

With reference to FIGS. 35 and 36, subsequently a first loop is made of the guide wire through the open portion of the gastric pocket and through the portions of the jejune and the stomach to be connected. An anastomotic device is inserted and locked on the guide means and dragged, by the same guide means, until abutting against the first portion to be connected and drawing it together with the second portion to be connected. This first sequence of steps ends with the performing of a gastro-jejuno anastomosis 88 and the formation of a first loop 86 of intestine.

Subsequently, a second loop of guide wire is made through the open portion of the gastric pocket and through the two portions of the jejune to be connected. The path of the second loop can develop through the oesophagus and along the stomach and a tract of the intestine to one of the tissue portions to be connected; externally to the other tissue portion to be connected and from there along the intestine, through the gastro-jejuno anastomosis and the oesophagus. Or, both branches of the loop can pass through the gastro-jejuno anastomosis previously performed.

In this case also, an anastomotic device is inserted and locked in a direction on the guide means and dragged, by the same guide means, until it abuts against the first portion to be connected and draws it together the second portion to be connected. This second sequence of steps ends with the performing of an entero-entero anastomosis 94, the carrying out of a second ring 96 of intestine and the completion of the gastric pocket 100. A section line of the intestine between the two anastomoses upon completion of the method has been indicated by 98.

The passing of the guide means through the walls of the tissues to be connected can be performed by punching the wall (for example with radiofrequency needles) at the area intended to form the anastomosis, so that after the formation of the anastomosis, the continuity of the intestinal duct is reintegrated.

An anastomotic device suitable for that aim can be the one described in the present application, or anastomotic or positioning devices suitable for releasing an anastomotic ring to perform the anastomosis, or a circular slidable stapler on the guide means and cooperating with an anvil, also slidable on the guide means.

In accordance with a possible embodiment, the guide means and the anastomotic device (in particular an abutment portion 18) can be spaced apart from each other and suitable for being mutually associated upon use. Or, a guide means can be provided in which the anastomotic device (and in particular the abutment portion 18) is pre-assembled or integrated on the guide means, so that it can be dragged in a direction and withdrawn in the opposite direction.

Furthermore, during insertion, in the case at least two guide wires are provided, the guide wires can be at least partially placed beside at a certain distance one from the other, or placed beside and approximated. In this case, by providing an insertion device, the guide wires can be introduced by means of a same operative channel, placed beside and approximated, so as to pass through the first tissue portion at a common opening. Optionally, during this step the distal ends of the guide wires can be mutually connected. They will be optionally split when the loop has been made.

As in the previous case, this method allows to reduce the mortality risks in the case of gastro-intestinal by-passes and to considerably minimize the intervention times. The preservation of the continuity of the intestine until the completion of the two anastomoses allows for the simultaneous assessment of both. Furthermore, in virtue of the approximated arrangement of the two anastomoses, the surgical field is restricted to the upper area of the abdomen.

To the preferred embodiment of the devices and methods above described, one skilled in the art, aiming at meeting contingent and specific needs, will be able to bring a number of modifications, adaptations and substitutions of elements with other functionally equivalent elements, without however departing from the scope of the following claims.

What is claimed is:

1. A method for performing anastomoses in tracts of the digestive tube, the method comprising the steps of:

introducing, through a natural orifice or other luminal structures, two guide wires (A, B) extending between proximal end portions (A', B') and distal end portions (A", B") and defining a guide wire loop passing through a first tissue portion (12) and through a second tissue portion (14) in which the anastomosis has to be performed, inserting along the two guide wires (A, B) an anastomotic device (10) comprising a ring-shaped abutment portion (18) having a central passage opening (38) suitable for the abutment against a surface of said first tissue portion (12) and a ring-shaped locking portion (20) having a central passage opening (36) and suitable for being placed opposite the abutment portion (18) with respect to the first and the second tissue portion (12, 14), said locking portion (20) and said abutment portion (18) being mutually connectable through the approximated first and second tissue portions (12, 14) to keep them close to each other, in which the abutment portion forms two channels (34) located outside the central passage opening (36) on two opposite sides thereof and passing through the abutment portion (18) for receiving respectively one of two guide wires (A, B), in which said abutment portion (18) is adapted to be locked in one direction on said two guide wires (A, B) so that the abutment portion can be dragged by said guide wires until reaching the first tissue portion (12) and said guide wires can be withdrawn from the abutment portion in an opposite direction, inserting and unidirectional locking said abutment portion (18) on said two guide wires and dragging the abutment portion to the anastomotic site by pulling one of the free ends of the loop until the abutment portion is abutted and partially inserted in the first portion (12) of the tissue, further dragging the abutment portion, together with the first tissue portion (12), until the first tissue portion is approximated to the second tissue portion (14), inserting said locking portion (20) of the anastomotic device (10) on the guide wires (A, B) and pushing the locking portion (20) along the guide wires (A, B) towards the abutment portion (18) and performing an anastomosis.

2. The method according to claim 1, in which the portion (20) of the anastomotic device (10) is snap fitted on the abutment portion (18) of the anastomotic device (10).

* * * * *